(12) United States Patent

Petersen et al.

(10) Patent No.: US 9,109,042 B2
(45) Date of Patent: Aug. 18, 2015

(54) DELAYING THE PROGRESSION OF DIABETES

(75) Inventors: Bryon E. Petersen, Gainesville, FL (US); Seh-Hoon Oh, Gainesville, FL (US); Thomas Shupe, Mocksville, NC (US); Houda Darwiche, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/116,368

(22) PCT Filed: May 8, 2012

(86) PCT No.: PCT/US2012/036967
§ 371 (c)(1),
(2), (4) Date: Jun. 5, 2014

(87) PCT Pub. No.: WO2012/154756
PCT Pub. Date: Nov. 15, 2012

(65) Prior Publication Data
US 2014/0303079 A1    Oct. 9, 2014

Related U.S. Application Data

(60) Provisional application No. 61/483,715, filed on May 8, 2011, provisional application No. 61/512,293, filed on Jul. 27, 2011, provisional application No. 61/514,965, filed on Aug. 4, 2011.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 15/11* | (2006.01) | |
| *C07K 14/47* | (2006.01) | |
| *A61K 38/17* | (2006.01) | |
| *A61K 45/06* | (2006.01) | |
| *A61K 31/7088* | (2006.01) | |
| *C12N 15/113* | (2010.01) | |

(52) U.S. Cl.
CPC ............ *C07K 14/47* (2013.01); *A61K 31/7088* (2013.01); *A61K 38/1709* (2013.01); *A61K 45/06* (2013.01); *C12N 15/113* (2013.01); *C12N 2310/14* (2013.01)

(58) Field of Classification Search
USPC .......................................... 514/44; 536/24.5
See application file for complete search history.

(56) References Cited

PUBLICATIONS

Oh et al. (Stem Cells and Development, 2009 vol. 18, No. 1:37-47).*
RIKEN Genome Exploration Research Group Phase II Team and the FANTOM Consortium (Nature, 2001, vol. 409:685-690).*
Unnamed protein product [Mus musculus], GenBank: BAC27208, downloaded from http://www.ncbi.nlm.nih.gov/protein/26326929 on Jul. 29, 2014.*
Oh et al. (Pancreas. 2012, vol. 41(1):22-30).*
Oh, Seh-Hoon et al., "Adult bone marrow-derived cells trans-differentiating into insulin-producing cells for the treatment of type I diabetes", Laboratory Investigation, 2004, vol. 84, pp. 607-617.
Oh, Seh-Hoon et al., "Detection of Transketolase in Bone Marrow-Derived Insulin-Producing Cells: Benfotiamine Enhances Insulin Synthesis and Glucose Metabolism", Stem Cells and Development, 2009, vol. 18, No. 1, pp. 37-45.
Oh, Seh-Hoon et al., "Characterization of a novel functional protein in the pancreatic islet: IHoP regulation of glucagon synthesis in alpha-cells", Pancreas, Jan. 2012, vol. 41(1), pp. 22-30.

* cited by examiner

*Primary Examiner* — Terra C Gibbs
(74) *Attorney, Agent, or Firm* — Timothy H. Van Dyke; Beusse, Wolter, Sanks & Maire, PLLC

(57) ABSTRACT

Type-1 diabetes (T1 D) results from the autoimmune recognition of insulin producing β-cells within the pancreatic islet. The present application discloses a new protein, islet homeostasis protein (IHoP), that has a role in glucagon synthesizing-cell functions, and in post-onset T1 D islet differential expression of IHoP. Methods of delaying the onset of diabetes are disclosed, as well as compositions including an iHoP modulating agent. Also disclosed are methods of screening for iHoP modulating agents.

16 Claims, 13 Drawing Sheets

MARGSVSDEEMMELREAFAKVDTDGKGYISCNELNDLFKAACLPLPGYRVREITENLMATGDLD
QDGKISFDEFIKVFHGLKSTEVAKTFRKAINKKEGICAIGGTSEQSSVGTQHSYSEEEKYAFVN
WINKALENDPDCRHVIPMNPNTDDLFNAVGDGIVLCKMINLSVPDTIDERTINKKKLTPFTIQE
NLNLALNSASAIGCHVVNIGAEDLKEGKPYLVLGLLWQVIKIGLFADIELSRNEALIALLREGE
SLEDLMKLSPEELLLRWANYHLENAGCTKITNFSTDIKDSKAYYHLLEQVAPKGDEEGIPAVVI
DMSGLREKDDIQRAECMLQQAERLGCRQFVTATDVVRGNPKLNLAFIANLFNKYPALHKPENQD
IDWGALEGETREERTFRNWMNSLGVNPRVNHLYSDLSDALVIFQLYEKIKVPVDWNRVNKPPYP
KLGGNMKKLENCNYAVDLGKNQAKFSLVGIAGQDLNEGNRTLTLALVWQLMRRYTLNILEDIGG
GQKVNDDIIVNWVNTTLKEAQKSSSIASFKDPKISTSLPVLDLIDAIQPGSINYDLLKTENLDD
EEKLNNAKYAISMARKIGARVYALPEDLVEVNPKMVMTVFACLMGKGMKRV

FIG. 7 (Protein Sequence for iHoP)

FIG. 8 nucleotide sequence of iHoP

```
   1 gtagatctga aggactgggg tttctgacca cacagcagtg ctgctgacac agaggacagt
  61 ttctctacca ggtctgtcac ctaaagcagt gaaaatggcc agaggatccg tgtctgacga
 121 agaaatgatg gagctcagag aggcttttgc caaagttgat accgatggca aaggatacat
 181 cagctgcaat gagctaaatg acttgttcaa ggccgcctgc ctgcctctgc ctgggtaccg
 241 agtgagagaa atcacagaaa acctgatggc cacaggtgat ctggaccaag atggaaagat
 301 cagctttgat gagtttatca aggtcttcca tggcttaaaa agcaccgagg ttgccaaaac
 361 cttccgaaaa gctatcaaca agaaggaagg gatctgtgcg attggcggca cctctgagca
 421 gtccagcgtt ggtacccagc actcttactc agaggaagaa aagtatgcct ttgtcaactg
 481 gataaacaaa gccctggaga atgacccga ctgccggcat gtcatcccca tgaaccccaa
 541 caccgacgat ctcttcaatg ctgtaggcga tggcatagtt ctttgtaaaa tgatcaacct
 601 gtctgtgcca gacacgattg acgagagaac gatcaacaag aaaaagctca caccattcac
 661 cattcaggaa aacttgaact ggctctgaa ctctgcctct gccattgggt gccacgtggt
 721 taatataggg gccgaggacc tgaaggaggg caagccttac ctggtcctgg gacttttgtg
 781 gcaagtcatc aagattgggt tgtttgctga cattgaactc agcagaaatg aagctctgat
 841 tgctcttttg agagaaggag agagcctaga ggatttgatg aagttgtctc ctgaagaact
 901 cctgctgcgg tgggctaact accacctaga aaacgcaggc tgcaccaaaa tcaccaactt
 961 cagcaccgac atcaaggact ccaaagctta ttaccacctg ctcgagcaag tggctccaaa
1021 aggagatgaa gaaggatcc cggcggttgt gattgacatg tcaggactga gggagaagga
1081 tgacatccag agggcagagt gcatgctgca acaggcggag aggctgggct gccggcagtt
1141 tgtcacagct actgatgttg tccgagggaa ccccaagttg aacctggcct tcattgccaa
1201 cctcttcaac aaatacctg ccttacacaa accagagaac caggacattg actgggggc
1261 tctcgaaggt gagacgaggg aagagcggac cttcaggaat tggatgaact ccctgggcgt
1321 taacccgcgc gtcaatcact gtacagcga cttatcggat gccttagtca tcttccagct
1381 ctatgagaag atcaaagtcc ctgttgattg aacagagta aacaagcctc catacccaa
1441 gctgggggc aatatgaaaa agctggagaa ctgtaattat gcagtggacc tggggaagaa
1501 tcaagctaaa ttctccctgg ttggcatcgc aggacaagac ctcaatgaag gaaaccgaac
1561 tctcacgctg gcattggttt ggcagctcat gagaaggtac acactgaata tcctggaaga
1621 tatcggaggt ggacagaagg tcaatgatga cattattgtc aactgggtga atacgacctt
1681 gaaggaggca cagaaaagct catccattgc tagcttcaag gacccaaaga tcagtaccag
1741 cctcccggtt ctggatctca ttgacgccat tcagccaggt tccataaact atgaccttct
1801 aaagacagaa aacctggatg atgaagagaa actcaacaat gcaaagtatg ccatctctat
1861 ggccagaaaa atcggagcaa gggtgtacgc cctcccagaa gacctggttg aagtgaaccc
1921 caaaatggtc atgacagtgt ttgcctgcct catggggaaa gggatgaaga gggtgtaagt
1981 cccagaggag taagccagaa atcgacacag acaagcctga gggggtcagc acatggtgct
2041 cccaggatgc agaggaccat tcaagccatt gcaaagtcct gaaccttgga gacattattt
2101 gaaattcaca catttcttca gccaagtagc ttctgctata attagcaata cgtgcttctc
2161 ttttgttgtt gttttttcag aagatgtact cgcctacaaa ttttttttt attctttgaa
2221 agtctacc
```

DELAYING THE PROGRESSION OF DIABETES

CROSS-REFERENCE TO RELATED APPLICATIONS

This application is related to U.S. Provisional Application 61/483,715 filed May 8, 2011; and U.S. Provisional Application 61/512,293 filed Jul. 27, 2011; and U.S. Provisional Application 61/514,965 filed Aug. 4, 2011 to which priority is claimed under 35 USC 119.

STATEMENT REGARDING FEDERALLY SPONSORED DEVELOPMENT

This invention was made with government support under grant number NIH NIDDKI: RO1 DK58614-05 and DK65096 awarded by the National Institutes of Health. Accordingly, the United States government has certain rights in this invention.

BACKGROUND

The pancreatic islets of Langerhans are composed of clusters of four cell types that synthesize various peptide hormones, including glucagon (α-cells), insulin (β-cells), somatostatin (δ-cells) and pancreatic polypeptide (PP-cells).[1] These different cell types are in close proximity to one another and primarily produce hormones to be circulated in blood (effects of endocrine) and secretion hormones of each cell type exert actions on adjacent cells within the islet (effects of paracrine).[2,3] These hormones release regulated nutrient control for management of tissue metabolism and the blood levels of glucose, fatty acids, triglycerides and amino acids. The maintenance of blood glucose levels requires production and secretion of both insulin and glucagon, which are closely regulated during glucose tolerance; these two hormones work in concert and stimulate glycogenolysis and gluconeogenesis in the presence or absence of nutrient intake.[4] The function of glucagon has been opposed by the action of insulin in peripheral tissues, predominantly the liver. It also regulates both islet α-cell proliferation and survival.[5] Glucagon release is normally stimulated as blood glucose concentrations fall, a response that is progressively diminished in type-1 diabetes.[6,7] Pathologically, insulin deficient islets still contain a normal complement of glucagon-secreting α-cells.[8] The glucagon may be the key counter regulatory hormone responsible for opposing the glucose-lowering effect of insulin, and may represent a therapeutic-target for the treatment of type-1 diabetes.[9]

The increasing incidence of type-1 diabetes throughout the world has generated considerable interest in developing both better diagnostic techniques and treatments that would restore glucose responsiveness and insulin secretion, as well as methods for prevention of development of diabetic mellitus by immune suppression. Several researchers have found approaches to the prevention and treatment of diabetes by using immunosuppressive and immunomodulatory agents such as insulin,[10] GAD65,[11] DiaPeP227,[12] anti-CD3,[13] mycophenolate mofetil,[14] daclizumab[15] and anti-CD20.[16] Cell therapy using stem cells and their progeny is a promising new approach that may be capable of addressing many unmet medical needs.[17] The transplantation of donor islet has been a key of treatment of type-1 diabetes mellitus, however after transplanted some patients still need to insulin injection.[18] Various endeavors, including transplantation of in vitro-differentiated islet-like cells,[19] transplantation of stem cells-derived insulin producing cells[20,21] and combination of stem cells therapy with a pharmacological approach[22] have been tested. These studies suggest that with the progression of stem cell research, new methods for the treatment of diseases such as diabetes mellitus may be possible. However the pathogenesis of type-1 diabetes as well as the mechanisms by which the above agents act is still unclear. Further study will be required to develop new approaches for the diagnosis and prevention of type-1 diabetes.

SUMMARY

In this study, the inventors recently identified an unknown functional protein in BM-derived IPCs and demonstrated its function. This protein was previously termed, unnamed protein product,[23] but the inventors now refer to it as Islet Homeostasis Protein, or IHoP. BM-derived IPCs and isolated pancreatic islets expressed the IHoP gene, and it co-localized within the glucagon synthesizing α-cells of the islets. The inventors provide knockdown expression of IHoP by siRNA data indicating that IHoP's role of glucagon synthesis in the α-cells, leads to control of insulin synthesis by β-cell. Finally, the inventors show that IHoP positive cells were increased in the pancreatic islet of NOD mice, and similar data was obtained in pre-onset diabetic patients. However, the post-onset-type-1 diabetic islets were negative for IHoP expression. These data suggest that IHoP may work to regulate islet homeostasis by (directly or indirectly) regulating expression of other pancreatic molecules such as glucagon.

BRIEF DESCRIPTION OF THE DRAWINGS

FIG. 7: relates to the amino acid sequence of iHoP (SEQ ID NO: 3).

FIG. 8: relates to a nucleic acid sequence encoding iHoP (SEQ ID NO: 4).

DETAILED DESCRIPTION

Figure 1:
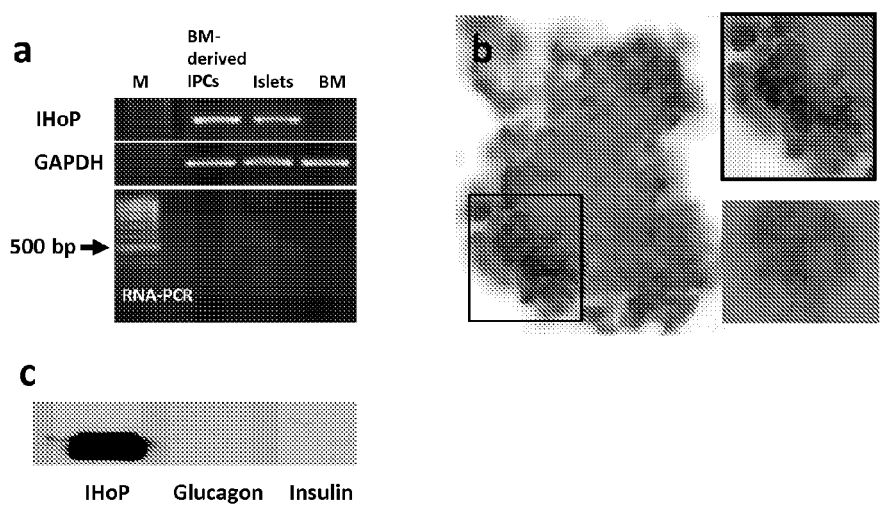
FIG. 1: Detection of IHoP in the pancreatic islets. (a) RT-PCR analysis for expression of IHoP (510 bp) in BM-derived IPCs, isolated rat pancreatic islets (islets) and undifferentiated BM cells (BM). GAPDH (580 bp) was used as an internal control. To test for DNA contamination, RNA samples were amplified using IHoP primers without reverse transcription (RNA-PCR). M indicates 100 bp ladder. (b) In situ hybridization of IHoP mRNA in the isolated normal rat pancreatic islets. The islets are positive for IHoP mRNA expression (purple) and counter stained with nuclear fast red. Black box top right is a higher magnification of the origin. The box at the right bottom is a negative control. Original magnification of b is 200×. (c) Western blot analysis to confirm specificity of IHoP antibody for IHoP peptide or pancreatic hormones. IHoP peptide (IHoP; 1 μg), Glucagon (1 μg) and insulin (1 μg) were loaded and transferred to a nylon membrane. Signal was detected by rabbit polyclonal anti-IHoP antibody. Data shown represent one of three experiments with similar results.

According to one embodiment, the invention pertains to a method of delaying the onset or treating diabetes by administering a therapeutically effective amount of an iHoP modulating agent to a subject in need. In a more specific embodiment, the invention pertains to administering iHoP according to a regimen that includes daily dosage of iHoP for a period of at least 24 hours, 48 hours, 3 days, 1 week or 2 weeks. Also, the iHoP may be included in a composition that comprises a pharmaceutically acceptable carrier.

According to another embodiment, the invention pertains to treating a pre-diabetic state in a subject.

In one embodiment, the invention pertains to a method of delaying the onset of diabetes by administering an iHoP modulating agent to a patient in need. The modulating agent may be an agent produced by a delivery vector that is introduced into the patient. The delivery vector may include a polynucleotide sequence that encodes the modulating agent. The delivery vector may be a viral or non-vector as is known in the art, including but not limited to, single-stranded and double-stranded nucleic acid vectors as well as DNA, RNA, and DNA/RNA chimeric vectors. Exemplary viral vectors include, but are not limited to, adenovirus, herpesvirus, lentivirus, parvovirus (e.g., AAV), baculovirus and Epstein Barr Virus vectors. Exemplary non-viral vectors include, but are not limited to, plasmid, phage, yeast artificial chromosomes (YACs), Bacterial Artificial Chromosomes (BACs), and naked DNA vectors (e.g., by liposomal delivery), or synthetic nucleotide vectors (e.g., vectors that are generated by PCR methods or oligonucleotide synthesis, as are known in the art). In one particular embodiment, the delivery vector is an adeno-associated virus (AAV) vector, e.g., in the form of AAV viral particles. In another embodiment, the delivery vector is a plasmid. The delivery vectors described herein may be used in both in vitro and in vivo studies. For example, in in vitro studies, the efficiency of the plasmid transfection can be monitored by GFP expression and the small peptide activity can be evaluated by a suitable biological assay. In a specific embodiment, the modulating agent is an iHoP disrupting molecule produced from the delivery vector, including but not limited to, is an RNA interference molecule described below, an antisense molecule, or a ribozyme targeting iHoP related RNA. Alternatively, the iHoP disrupting molecule is an antibody directed to the iHoP protein.

According to certain embodiments, in the case of treating a prediabetic state, a patient in need is one who is experiencing two or more of the following symptoms: ketoacidosis, a state of metabolic dysregulation characterized by the smell of acetone; a rapid, deep breathing known as Kussmaul breathing; nausea; vomiting and abdominal pain; polyuria (frequent urination); polydipsia (increased thirst); polyphagia (increased hunger), increased or decreased insulin levels, or elevated serum glucose, or a combination thereof. In a more specific embodiment, the patient in need for treating a pre-diabetic state is a patient that has impaired glucose tolerance, i.e., fasting glucose levels from 100 to 125 mg/dL (5.6 to 6.9 mmol/L), also referred to as impaired fasting glucose. Additionally, or alternatively, subjects with plasma glucose at or above 140 mg/dL (7.8 mmol/L), but not over 200 mg/dL (11.1 mmol/L), two hours after a 75 g oral glucose load are considered to have impaired glucose tolerance. In still the prediabetic state relates to an impaired fasting glucose level (equal to or greater than 100 mg/dL) or glucose intolerance (greater than 140 mg/dL two hours post premeasured glucose drink).

According to certain embodiments, in the case of preventing or delaying the onset of diabetes, a patient in need is one who is experiencing ketoacidosis, a state of metabolic dysregulation characterized by the smell of acetone; a rapid, deep breathing known as Kussmaul breathing; nausea; vomiting and abdominal pain; polyuria (frequent urination); polydipsia (increased thirst); polyphagia (increased hunger), increased or decreased insulin levels, or elevated serum glucose, or a combination thereof. In a more specific embodiment, the patient in need for prevention or delaying onset is a patient that has impaired glucose tolerance, i.e., fasting glucose levels from 100 to 125 mg/dL (5.6 to 6.9 mmol/L), also referred to as impaired fasting glucose. Additionally, or alternatively, subjects with plasma glucose at or above 140 mg/dL (7.8 mmol/L), but not over 200 mg/dL (11.1 mmol/L), two hours after a 75 g oral glucose load are considered to have impaired glucose tolerance.

According to certain aspects, the invention pertains to a method of treating or delaying the onset of a condition. The condition may be selected from the group consisting of: diabetes mellitus, gestational diabetes, genetic defects of β-cell function, genetic defects in insulin action, diseases of the exocrine pancreas, endocrinopathies, drug or chemical-induced, infections, other genetic syndromes associated with diabetes, a pre-diabetic state, and metabolic syndrome. In one aspect, the condition is diabetes mellitus, including type I and/or type II.

A pharmacologically acceptable carrier which may be employed for producing a composition of the present invention may, for example, be various organic and inorganic carrier materials employed customarily as pharmaceutical materials such as excipients, lubricants, binders and disintegrants in a solid formulation, solvents, dissolution aids, suspending agents, isotonicity imparting agents, buffering agents and analgesic agents in a liquid formulation. Furthermore, other additives such as ordinary preservatives, antioxidants, colorants, sweeteners, adsorbents, wetting agents may also be added in suitable amounts.

An excipient may be, for example, lactose, sugar, D-mannitol, starch, corn starch, crystalline cellulose, light silicate anhydride and the like. A lubricant may, for example, be magnesium stearate, calcium stearate, talc, colloidal silica and the like.

A binder may be, for example, crystalline cellulose, sugar, D-mannitol, dextrin, hydroxypropyl cellulose, hydroxypropylmethyl cellulose, polyvinyl pyrrolidone, starch, sucrose, gelatin, methyl cellulose, sodium carboxymethyl cellulose and the like.

A disintegrant may be, for example, starch, carboxymethyl cellulose, calcium carboxymethyl cellulose, sodium carboxymethyl starch, L-hydroxypropyl cellulose and the like.

A solvent may be, for example, water for injection, alcohol, propylene glycol, macrogol, sesame oil, corn oil, olive oil and the like.

A dissolution aid may be, for example, polyethylene glycol, propylene glycol, D-mannitol, benzyl benzoate, ethanol, trisaminomethane, cholesterol, triethanolamine, sodium carbonate, sodium citrate and the like.

A suspending agent may be, for example, a surfactant such as stearyl triethanolamine, sodium lauryl sulfate, laurylaminopropionic acid, lecithin, benzalkonium chloride, benzethonium chloride, glycerin monostearate and the like; hydrophilic polymer such as polyvinyl alcohol, polyvinyl pyrrolidone, sodium carboxymethyl cellulose, methyl cellulose, hydroxymethyl cellulose, hydroxyethyl cellulose, hydroxypropyl cellulose and the like.

An isotonicity imparting agent may be, for example, glucose, D-sorbitol, sodium chloride, glycerin, D-mannitol and the like.

A buffering agent may be, for example, a buffer solution of a phosphate, acetate, carbonate, citrate and the like.

An analgesic may be, for example, benzyl alcohol.

A preservative may be, for example, a p-oxybenzoate, chlorobutanol, benzyl alcohol, phenethyl alcohol, dehydroacetic acid, sorbic acid and the like.

An antioxidant may, for example, be a sulfite, ascorbic acid, lipoic acid, α-tocopherol, EGCG and the like.

According to other embodiments, the invention pertains to compounds and compositions of the used in conjunction with other therapeutic agents for co-therapies, partially or completely, in place of other therapeutic agents. Thus, in certain embodiments, the invention provides methods for treating diabetes by administering to the patient in need thereof an effective amount of the compounds and/or compositions described herein. For example, the patient can be administered an effective amount of an iHoP modulating agent. In yet another embodiment, the patient can be administered an effective amount of an iHoP modulating agent, and, at least one therapeutic agent, including but not limited to, such as, for example, an antidiabetic compound and an antioxidant, and combinations of two or more thereof. The iHoP modulating agent and/or therapeutic agents can be administered separately or as components of the same composition in one or more pharmaceutically acceptable carriers.

Suitable antidiabetic compounds include but are not limited to, acarbose, acetohexamide, buformin, carbutamide, chlorpropamide, glibornuride, gliclazide, glimepiride, glipizide, gliquidone, glisoxepid, glyburide, glybuthiazol(e), glybuzole, glyhexamide, glymidine, glypinamide, insulin, metformin, miglitol, nateglinide, phenbutamide, phenformin, pioglitazone, repaglinide, rosiglitazone, tolazamide, tolbutamide, tolcyclamide, troglitazone, voglibose, and the like. Suitable antidiabetic compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable antioxidants include, but are not limited to, small-molecule antioxidants and antioxidant enzymes. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like. Suitable antioxidant enzymes include, but are not limited to, superoxide dismutase, catalase, glutathione peroxidase, NADPH oxidase inhibitors, such as, for example, apocynin, aminoguanidine, ONO 1714, S17834 (benzo[b]pyran-4-one derivative), and the like; xanthine oxidase inhibitors, such as, for example, allopurinol, oxypurinol, amflutizole, diethyldithiocarbamate, 2-styrylchromones, chrysin, luteolin, kaempferol, quercetin, myricetin, isorhamnetin, benzophenones such as 2,2',4,4'-tetrahydroxybenzophenone, 3,4,5,2',3',4'-hexahydroxybenzophenone and 4,4'-dihydroxybenzophenone; benzothiazinone analogues such as 2-amino-4H-1,3-benzothiazine-4-one, 2-guanidino-4H-1,3-benzothiazin-4-one and rhodanine; N-hydroxyguanidine derivative such as, PR5 (1-(3,4-dimethoxy-2-chlorobenzylideneamino)-3-hydroxyguanidine); 6-formylpterin, and the like. The antioxidant enzymes can be delivered by gene therapy as a viral vector and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the antioxidants are apocynin, hydralazine compounds and superoxide dimutase mimetics. an iHoP protein might be co-administrated with insulin to regulate blood glucose more effectively within a short period of time.

When administered separately, the an iHoP modulating agent and/or other therapeutic agent can be administered about the same time as part of the overall treatment regimen, i.e., as a combination therapy. "About the same time" includes administering the an iHoP protein, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of an iHoP protein and/or at least one therapeutic agent, they can also be used in combination with one or more additional compounds which are known to be effective against the specific disease state targeted for treatment. The therapeutic agents can be administered simultaneously with, subsequently to, or prior to administration of the an iHoP protein.

The compounds and compositions of the invention can be administered by any available and effective delivery system including, but not limited to, orally, bucally, parenterally, by inhalation, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. In one embodiment of the invention the an iHoP protein is administered orally, parentally or by inhalation.

1. Screening Methods

The invention provides assays for screening test compounds which bind to or modulate the activity of a iHoP polypeptide or bind to and inhibit or affect expression of a iHoP polynucleotide. A test compound preferably binds to an iHoP polypeptide. More preferably, a test compound decreases or increases iHoP activity by at least about 10, preferably about 50, more preferably about 75, 90, or 100% relative to the absence of the test compound.

1.1. Test Compounds

Test compounds relate to agents that potentially have therapeutic activity, i.e., bind to or modulate the activity of a iHoP polypeptide or bind to or affect expression of a iHoP polynucleotide. Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. NatL. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994).

1.2. High Throughput Screening

Test compounds can be screened for the ability to bind to and inhibit iHoP polypeptides or polynucleotides or to affect iHoP activity or iHoP gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format. Alternatively, "free format assays," or assays that have no physical barrier between samples, can be used.

1.3. Binding Assays

For binding assays, the test compound is preferably, but not necessarily, a small molecule which binds to and occupies, for example, the active site of the iHoP polypeptide, such that normal biological activity is prevented. Examples of such small molecules include, but are not limited to, small peptides or peptide-like molecules.

In binding assays, either the test compound or the iHoP polypeptide can comprise a detectable label, such as a fluorescent, radioisotopic, chemiluminescent, or enzymatic label, such as horseradish peroxidase, alkaline phosphatase, or luciferase. Detection of a test compound which is bound to the iHoP polypeptide can then be accomplished, for example, by direct counting of radioemission, by scintillation counting, or by determining conversion of an appropriate substrate to a detectable product.

Those skilled in the art equipped with teachings herein will appreciate that there are multiple conventional methods of detecting binding of a test compound. For example, binding of a test compound to a iHoP polypeptide can be determined without labeling either of the interactants. A microphysiometer can be used to detect binding of a test compound with a iHoP polypeptide. A microphysiometer (e.g., CYTOSENSOR™) is an analytical instrument that measures the rate at which a cell acidifies its environment using a light-addressable potentiometric sensor (LAPS). Changes in this acidification rate can be used as an indicator of the interaction between a test compound and a iHoP polypeptide (McConnell et al., Science 257, 19061912, 1992).

In another alternative example, determining the ability of a test compound to bind to a iHoP polypeptide can be accomplished using a technology such as real-time Bimolecular Interaction Analysis (BIA) (Sjolander & Urbaniczky, Anal Chem. 63, 23382345, 1991, and Szabo et al., Curr. Opin. Struct. Biol. 5, 699705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a iHoP polypeptide can be used as a "bait protein" in a two-hybrid assay or three-hybrid assay (see, e.g., U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and Brent WO94/10300), to identify other proteins which bind to or interact with the iHoP polypeptide and modulate its activity.

In many screening embodiments, it may be desirable to immobilize either the iHoP polypeptide (or polynucleotide) or the test compound to facilitate separation of bound from unbound forms of one or both of the interactants, as well as to accommodate automation of the assay. Thus, either the iHoP polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the iHoP polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a iHoP polypeptide (or polynucleotide) can be accomplished in any vessel suitable for containing the reactants. Examples of such vessels include microtiter plates, test tubes, and microcentrifuge tubes.

In a specific embodiment, the iHoP polypeptide may be a fusion protein comprising a domain that allows the iHoP polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the nonadsorbed iHoP polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a iHoP polypeptide (or polynucleotide) or a test compound can be immobilized utilizing conjugation of biotin and streptavidin. Biotinylated iHoP polypeptides (or polynucleotides) or test compounds can be prepared from biotinNHS (Nhydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a iHoP polypeptide, polynucleotide, or a test compound, but which do not interfere with a desired binding site, such as the active site of the iHoP polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the iHoP polypeptide or test compound, enzyme-linked assays which rely on detecting an activity of the iHoP polypeptide, and SDS gel electrophoresis under non-reducing conditions.

Screening for test compounds which bind to a iHoP polypeptide or polynucleotide also can be carried out in an intact cell. Any cell which comprises a iHoP polypeptide or polynucleotide can be used in a cell-based assay system. A iHoP polynucleotide can be naturally occurring in the cell or can be introduced using techniques such as those described above. Binding of the test compound to a iHoP polypeptide or polynucleotide is determined as described above.

1.4. Enzyme Assays

Test compounds can be tested for the ability to increase or decrease the iHoP activity of a iHoP polypeptide. iHoP activity can be measured such as by that described in the Examples. Enzyme assays can be carried out after contacting either a purified iHoP polypeptide, a cell membrane preparation, or an intact cell with a test compound. A test compound which decreases TGS activity of a iHoP polypeptide by at least about 10, preferably about 50, more preferably about 75, 90, or 100% is identified as a potential therapeutic agent for decreasing iHoP activity. A test compound which increases TGS iHoP polypeptide by at least about 10, preferably about 50, more preferably about 75, 90, or 100% is identified as a potential therapeutic agent for increasing TGS activity.

1.5. Gene Expression

In another embodiment, test compounds which increase or decrease iHoP gene expression are identified. A iHoP polynucleotide (for example, see FIG. 8) is contacted with a test compound, and the expression of an RNA or polypeptide product of the iHoP polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of iHoP mRNA or polypeptide expression in the cells can be determined by methods well known in the art for detecting mRNA or polypeptide. Either qualitative or quantitative methods can be used. The presence of polypeptide products of a iHoP polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a iHoP polypeptide.

Such screening can be carried out either in a cell-free assay system or in an intact cell. Any cell which expresses a iHoP polynucleotide can be used in a cell-based assay system. The iHoP polynucleotide can be naturally occurring in the cell or can be introduced using techniques such as those described above. Either a primary culture or an established cell line, such as CHO or human embryonic kidney 293 cells, can be used.

2. Pharmaceutical Compositions

The invention also pertains to pharmaceutical compositions comprising one or more therapeutic agents that have therapeutic activity. Typically, therapeutic activity pertains to modulation of iHoP activity, expression or effects. More typically, for therapeutic applications, therapeutic activity pertains to down-regulation of activity, expression or effects of iHoP. Other therapeutic agents include iHop itself (see for example, FIG. 7). Therapeutic agents include those that are identified by screening methods that utilize iHoP polypeptides and/or polynucleotides. Pharmaceutical compositions of the invention can comprise, for example, therapeutic agents identified by a screening method embodiment described herein, which are identified by their ability to bind to or affect activity of iHoP polypeptides, or bind to and/or affect expression iHoP polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Accordingly, some examples of an agent having therapeutic activity, such as delaying the onset of diabetes, as described herein, or otherwise modulating activity of iHoP, include but are not limited to an antisense nucleic acid molecule, small molecule iHoP inhibitors, peptide inhibitors, a specific antibody, ribozyme, siRNA or a iHoP polypeptide binding molecule targeted to iHoP, or an antibody specific to iHoP. Agents can be used in an animal model to determine the efficacy, toxicity, or side effects of treatment with such an agent. In addition, compositions may include a conjunctive agent in addition to the therapeutic agents of the present invention.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about 106 cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes conventionally used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

Alternatively, the modulating agent may be an agent produced by a delivery vector that is introduced into the patient. The delivery vector may include a polynucleotide sequence that encodes the modulating agent. The delivery vector may be a viral or non-vector as is known in the art, including but not limited to, single-stranded and double-stranded nucleic acid vectors as well as DNA, RNA, and DNA/RNA chimeric vectors. Exemplary viral vectors include, but are not limited to, adenovirus, herpesvirus, lentivirus, parvovirus (e.g., AAV), baculovirus and Epstein Barr Virus vectors. Exemplary non-viral vectors include, but are not limited to, plasmid, phage, yeast artificial chromosomes (YACs), Bacterial Artificial Chromosomes (BACs), and naked DNA vectors (e.g., by liposomal delivery), or synthetic nucleotide vectors (e.g., vectors that are generated by PCR methods or oligonucleotide synthesis, as are known in the art). In one particular embodiment, the delivery vector is an adeno-associated virus (AAV) vector, e.g., in the form of AAV viral particles. In another embodiment, the delivery vector is a plasmid. The delivery vectors described herein may be used in both in vitro and in vivo studies. For example, in in vitro studies, the efficiency of the plasmid transfection can be monitored by GFP expression and the small peptide activity can be evaluated by a suitable biological assay. In a specific embodiment, the modulating agent is an iHoP disrupting molecule produced from the delivery vector, including but not limited to, is an sRNA, an miRNA, antisense molecule, or a ribozyme targeting iHoP related RNA. Alternatively, the iHoP disrupting molecule is an antibody directed to the iHoP protein.

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which modulates iHoP activity compared to that which occurs in the absence of the therapeutically effective dose.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

The effectiveness of the mechanism chosen to decrease the level of expression of a iHoP gene or the activity of a iHoP polypeptide can be assessed such as by hybridization of nucleotide probes to iHoP-specific mRNA, quantitative RT-PCR, immunologic detection of a iHoP polypeptide, or measurement of iHoP activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy.

3. Polypeptides iHoP polypeptides according to the invention comprise at least 12, 15, 25, 50, 75, 100, 125, 150, 175, 200, 225, 250 or 265 contiguous amino acids selected from the amino acid sequence shown in FIG. 7, or a biologically active variant thereof, as defined below. A iHoP polypeptide of the invention therefore can be a portion of a iHoP protein, a full-length iHoP protein, or a fusion protein comprising all or a portion of iHoP protein.

3.1 Biologically Active Variants iHoP polypeptide variants which are biologically active, i.e., regulate glucagon secretion, also are considered iHoP polypeptides for purposes of this application. Preferably, naturally or non-naturally occurring iHoP polypeptide variants have amino acid sequences which are at least about 55, 60, 65, or 70, preferably about 75, 80, 85, 90, 96, 96, or 98% identical to the amino acid sequence shown in FIG. 7 or a fragment thereof. Percent identity between a putative iHoP polypeptide variant and an amino acid sequence is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a iHoP polypeptide can be found using computer programs well known in the art, such as DNASTAR software. Whether an amino acid change results in a biologically active iHoP polypeptide can readily be determined by assaying for iHoP activity, as described for example, in the specific Examples, below.

3.2 Fusion Proteins

In some embodiments of the invention, it is useful to create fusion proteins. By way of example, fusion proteins are useful for generating antibodies against iHoP polypeptide amino acid sequences and for use in various assay systems. For example, fusion proteins can be used to identify proteins which interact with portions of a iHoP polypeptide. Protein affinity chromatography or library-based assays for protein-protein interactions, such as the yeast two-hybrid or phage display systems, can be used for this purpose. Such methods are well known in the art and also can be used as drug screens.

A iHoP polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of a iHoP sequence or of a biologically active variant, such as those described above. The first polypeptide segment also can comprise full-length iHoP protein.

The second polypeptide segment can be a full-length protein or a protein fragment. Proteins commonly used in fusion protein construction include galactosidase, glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the iHoP polypeptide-encoding sequence and the heterologous protein sequence, so that the iHoP polypeptide can be cleaved and purified away from the heterologous moiety.

Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

4. Polynucleotides

A iHoP polynucleotide can be single- or double-stranded and comprises a coding sequence or the complement of a coding sequence for a iHoP polypeptide. See for example FIG. 8. In view of the teachings herein, those skilled in the art can readily identify iHoP cognates, such as from different species.

Degenerate nucleotide sequences encoding iHoP polypeptides, as well as homologous nucleotide sequences which are at least about 50, 55, 60, 65, 60, preferably about 75, 90, 96, or 98% identical to the iHoP nucleotide sequence also are iHoP-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of iHoP polynucleotides which encode biologically active iHoP polypeptides also are iHoP polynucleotides.

4.1 Identification of Polynucleotide Variants and Homologs

Variants and homologs of the iHoP polynucleotides described above also are iHoP polynucleotides. Typically, homologous iHoP polynucleotide sequences can be identified by hybridization of candidate polynucleotides to known iHoP polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the iHoP polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Variants of iHoP polynucleotides or polynucleotides of other species can therefore be identified by hybridizing a putative homologous iHoP polynucleotide. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to iHoP polynucleotides or their complements following stringent hybridization and/or wash conditions also are iHoP polynucleotides. Stringent wash conditions are well known and understood in the art and are disclosed, for example, in Sambrook et al., MOLECULAR CLONING: A LABORATORY MANUAL, 2nd ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a iHoP polynucleotide having an iHoP nucleotide sequence shown or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5°\text{ C.} - 16.6(\log_{10}[\text{Na}^+]) + 0.41(\%G+C) - 0.63(\% \text{formamide}) - 600/l,$$

where l=the length of the hybrid in basepairs.
Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

4.2 Preparation of Polynucleotides

A naturally occurring iHoP polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated iHoP polynucleotides. For example, restriction enzymes and probes can be used to isolate polynucleotide fragments which comprises iHoP nucleotide sequences. Isolated polynucleotides are in preparations which are free or at least 70, 80, or 90% free of other molecules.

iHoP DNA molecules can be made with standard molecular biology techniques, using iHoP mRNA as a template. iHoP DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesize iHoP polynucleotides. The degeneracy of the genetic code allows alternate nucleotide sequences to be synthesized which will encode a iHoP polypeptide having, for example, or a biologically active variant thereof.

4.3 Expression of Polynucleotides

To express a iHoP polynucleotide, the polynucleotide can be inserted into an expression vector which contains the necessary elements for the transcription and translation of the inserted coding sequence. Methods which are well known to those skilled in the art can be used to construct expression vectors containing sequences encoding iHoP polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a iHoP enzyme polypeptide or iHoP modulating agent, including, but not limited to, a iHoP disrupting molecule. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a iHoP polypeptide, vectors based on SV40 or EBV can be used with an appropriate selectable marker.

5. Host Cells

According to certain embodiments of the subject invention, a iHoP polynucleotide will need to be inserted into a host cell, for expression, processing and/or screening. A host cell strain can be chosen for its ability to modulate the expression of the inserted sequences or to process the expressed iHoP polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express iHoP polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced iHoP sequences. Resistant clones of stably transformed cells can be proliferated using tissue culture techniques appropriate to the cell type. See, for example, ANIMAL CELL CULTURE, R. I. Freshney, ed., 1986.

5.1 Detecting Expression

A variety of protocols for detecting and measuring the expression of a iHoP polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a iHoP polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

5.2 Expression and Purification of Polypeptides

Host cells transformed with nucleotide sequences encoding iHoP polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode iHoP polypeptides can be designed to contain signal sequences which direct secretion of soluble iHoP polypeptides through a prokaryotic or eukaryotic cell membrane or which direct the membrane insertion of membrane-bound iHoP polypeptide.

6. Antibodies

Antibodies are referenced herein and various aspects of the subject invention utilize antibodies specific to iHoP polypeptide(s). As described above, one example of an therapeutic agent may pertain to an antibody. Any type of antibody known in the art can be generated to bind specifically to an epitope of a iHoP polypeptide. "Antibody" as used herein includes intact immunoglobulin molecules, as well as fragments thereof, such as Fab, F(ab')$_2$, and Fv, which are capable of binding an epitope of a iHoP polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a iHoP polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

7. Ribozymes

Ribozymes may be one category of compounds useful as therapeutic agents for modulating iHoP activity. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of a iHoP polynucleotide to generate ribozymes which will specifically bind to mRNA transcribed from the iHoP polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a iHoP RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate iHoP RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease iHoP expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

8. RNA Interference Molecules iHoP can be inhibited by a number of means including RNA interference. As used herein, the terms "interfering molecule" refer to all molecules, e.g., DNA, RNA or RNA-like molecules, that can affect expression of an iHoP protein. One example of rna interference molecules pertains to antisense molecules targeting an iHoP RNA transcription. Examples of other interfering RNA molecules include siRNAs, short hairpin RNAs (shRNAs), single-stranded siRNAs, microRNAs (miRNAs), and dicer-substrate 27-mer duplexes. Examples of "RNA-like" molecules include, but are not limited to, siRNA, single-stranded siRNA, microRNA, and shRNA molecules that contain one or more chemically modified nucleotides, one or more non-nucleotides, one or more deoxyribonucleotides, and/or one or more non-phosphodiester linkages. "Interfering molecules" also may include PMOs. PMOs have the same nucleic acid bases naturally found in RNA or DNA (i.e. adenine, cytosine, guanine, uracil or thymine), however, they are bound to morpholine rings instead of the ribose rings used by RNA. They may also linked through phosphorodiamidate rather than phosphodiester or phosphorothioate groups. This linkage modification eliminates ionization in the usual physiological pH range, so PMOs in organisms or cells are uncharged molecules. The entire backbone of a PMO is made from these modified subunits. Thus, siRNAs, single-strandedsiRNAs, shRNAs, miRNAs, and dicer-substrate 27-mer duplexes are subsets of "interfering RNAs" or "interfering RNA molecules."

In one embodiment, siRNA molecules can be prepared against a portion of iHoP according to the techniques provided in U.S Patent Publication 20060110440 and used as therapeutic compounds. As discussed above, agents can be developed to silence iHoP genes to achieve a therapeutic affect. In certain embodiments, silencing of human iHoP genes should be based on the sequences for two isoforms of the enzyme:

EXAMPLES

Example 1

Materials and Methods
Detection of IHoP Protein and mRNA

All procedures involving animals were conducted according to institutionally approved protocols and guidelines. The detection of IHoP protein in BM-derived IPCs was accomplished as previously reported. [22] Total RNA was isolated from the un-differentiated BM cells, BM-derived IPCs and isolated rat normal pancreatic islets[24] using RNA-Bee (Tel-Test, Inc. Friendswood, TX). 2 µg RNA was used for cDNA synthesis via reverse transcription. Also, confirm to DNA contamination in RNA, PCR samples were run without reverse transcribed-RNA using IHoP primers (RNA-PCR). The IHoP primers used were 5'-aag ttg aac ctg gcc tcc att-3' (SEQ ID NO: 1) (sense strand) and 5'-ctt caa ggt cgt att cac cca-3' (SEQ ID NO: 2) (anti-sense strand), which delineated a 510-bp product. PCR products (30 cycles) were directly sequenced using an AmpliTaq cycle sequencing kit (Perkin-Elmer Setus, Branchburg, NJ) for genetic confirmation.

IHoP-siRNA Transduction into In Vivo

The RNA interference (RNAi) has emerged as a powerful technology for studying gene functions in eukaryotes. RNAi is a post-transcriptional process triggered by the introduction of small interfering RNA (siRNA) which leads to gene silencing in a sequence-specific manner. [25-27] The design of IHoP-siRNA primers and scrambled-siRNA control were performed using a siRNA targeting program (Genescript, Piscataway, N.J.). IHoP-siRNA was amplified using psiRNA-hH1GFPzeo G2 kit (Invivogen, San Diego, Calif., USA). In vivo transduction of IHoP-siRNA or scrambled-siRNA (50 µg per animal) was performed per manufacturer's instructions using the in vivo jetPEi protocol (QBiogene, Irvine, Calif.). Fisher F344 female rats (age 8-10 weeks, 150-200 g) were purchased from Charles River Laboratories (Wilmington, Mass.) and maintained on standard laboratory chow and daily cycles of alternating 12 h light and dark. The rats were divided into 3 groups (n=3) one group was a non-treated control, the second group was injected with scramble-siRNA, and the final group was injected with IHoP-siRNA, all by tail vein injection.

Western Blot Analysis and Enzyme-Linked Immunosorbent Assay (ELISA)

For testing possible cross-reactions of the IHoP antibody the inventors prepared 1 µg each of glucagon, insulin and IHoP peptides, which were loaded and transferred onto a nylon membrane. The detection of IHoP on the membrane was followed by Western blotting, as detailed by Oh et al. [21] To determine insulin secretion, the cultured conditioned media were saved from INS-1 cells following high glucose challenge with glucagon or IHoP. Secretion of insulin into cultured media was detected by ELISA. ELISA was performed on the conditioned media to determine insulin secretion using the Rat insulin ELISA kit, and following the manufacturer's instructions (Crystal Chem Inc., Chicago, Ill.).

Cell Proliferation Assay

MTT [3-(4,5-dimethylthiazol-2-yl)-2,5-diphenyltetrazolium bromide; Sigma, St. Louis, Mo.] assay was performed as described previously by Mosmann. [28] Briefly, INS-1 cells were inoculated in a 96-well plate ($1 \times 10^4$ cells/well) and grown in INS-1 cell medium (Rosewell Park Memorial Institute-1640; Sigma) with 10% fetal bovine serum (FBS). [22] After 24 hours, the medium was replaced with 10% FBS supplemented INS-1 culture medium (positive control), serum-free INS-1 culture medium containing 0.5% bovine serum albumin (BSA; negative control), or 0.5% BSA medium with glucagon (1 µM) or IHoP (1 µM). The cells were cultured with glucagon and IHoP for 24, 48 and 72 hours, and then analyzed by spectrophotometry.

In Situ Hybridization with Digoxigenin Labeled DNA Probes

Isolated rat pancreatic islets were attached to slides glass and fixed for 15 min in 4% paraformaldehyde. The IHoP digoxigenin-labeled DNA probe (Roche, Indianapolis, Ind.) was then denatured at 80° C. for 5 min and applied to sections at 52° C. The hybridization procedure was continued as previously described. [21] Color development was performed at room temperature in buffer (Tris 100 mM, NaCl 100 mM and $MgCl_2$ 50 mM, pH 9.5) containing NBT and BCIP (Roche). Following signal development, slides were counterstained with nuclear fast red (Vector Laboratories, Burlingame, Calif.) and mounted in Cytoseal XYL (Richard-Allan Sci. Kalamazoo, Mich.).

Immunocytochemistry

Immunostaining on the rat normal pancreas, IHoP-siRNA transduced rat pancreas, NOD/wild type mice and human pre- and post-onset type-1 diabetic pancreas tissues was performed following previously described methods. [21,22] The following antibodies were used in this procedure: rabbit anti-insulin (Santa Cruz Biotechnology, Inc., Santa Cruz, Calif.), goat anti-glucagon (Santa Cruz), rabbit anti-glucagon (Dako, Carpinteria, Calif.), goat anti-C-peptide (Linco Research Inc., St. Charles, Mo.), anti-pancreatic polypeptide (Dako), goat anti-somatostatin (Santa Cruz) and rabbit anti-IHoP (prepared by GenScript Corp. Piscataway, N.J.). Alexa Fluor 488 or 568 donkey anti-rabbit and Alexa Flour 488 or 568 donkey anti-goat IgG, antigoat (1:500, Invitrogen) were used as secondary antibodies, respectively.

Briefly, the slides were blocked with peroxidase and avidin/biotin (Vector Lab. Burlingame, Calif.), after which they were incubated with primary antibody for 1 hour, followed by secondary antibody for 30 minutes. Detection was performed using Vector ABC kit (Vector Lab.) and 3,3'-diaminobenzidine tetrahydrochloreide (DAB) reagent (Dako). The test of apoptosis was performed using ApopTag Plus fluorescein in situ apoptosis detection kit (Chemicon, Temecula, Calif.). DAPI (Vector Lab.).

Statistical Analysis

All data shown represent one of at least three experiments with similar results. Values are expressed as the mean±standard deviation (S.D.). Statistical differences were determined by Student's t-test. Values at P<0.05 were considered to be statistically significant.

Results

Detection of IHoP in Insulin Producing Cells and Pancreatic Islets

The inventors have previously reported the detection of *Rattus Norvegicus* transketolase and *Mus Musculus* unnamed protein product[23] (gi 26326929; renamed Islet Homeostasis protein; IHoP) in BM-derived IPCs by protein sequence analysis (a protein of approximately 60 kDa).[22] When IHoP was detected in the BM-derived IPCs, the inventors focused on determining the function of IHoP within the pancreatic islets.

Confirmation of IHoP expression in undifferentiated BM cells, BM-derived IPCs and isolated rat normal pancreatic islets was accomplished by comparing IHoP gene expression via RT-PCR (FIG. 1*a*). Also, the inventors tested for DNA contamination in the RNA samples by RNA-PCR, but no bands were detected (bottom panel in FIG. 1*a*; RNA-PCR). IHoP mRNA was found in BM-derived IPCs and isolated rat pancreatic islets; however, undifferentiated BM cells did not express the IHoP gene. Also, the inventors examined at IHoP expression in isolated pancreatic islet utilizing in-situ hybridization. FIG. 1*b* shows the presence of IHoP mRNA in the cytoplasm of the pancreatic islets using a DIG-labeled IHoP-oligonucleotide probe. IHoP mRNA is clearly visible in a majority of the perimeter cells bordering the islets (FIG. 1*b*). These results indicate that IHoP expression is limited to a subset of cells within the islet, mostly likely the α-cells, as the β-cells are devoid of IHoP expression.

In addition, the inventors designed an antibody for the detection of IHoP which binds specifically to the c-terminus (GenScript Corp.). The inventors first confirmed that the IHoP antibody did not recognize pancreatic hormones such as glucagon and insulin by Western blot analysis (FIG. 1*c*). The antibody did not recognize glucagon or insulin and only recognized the IHoP peptide (FIG. 1*c*). These results indicated that IHoP may be a new functional protein as yet undefined within the islets of Langerhans.

Detection of IHoP in Normal Pancreatic Islets

Figure 2:
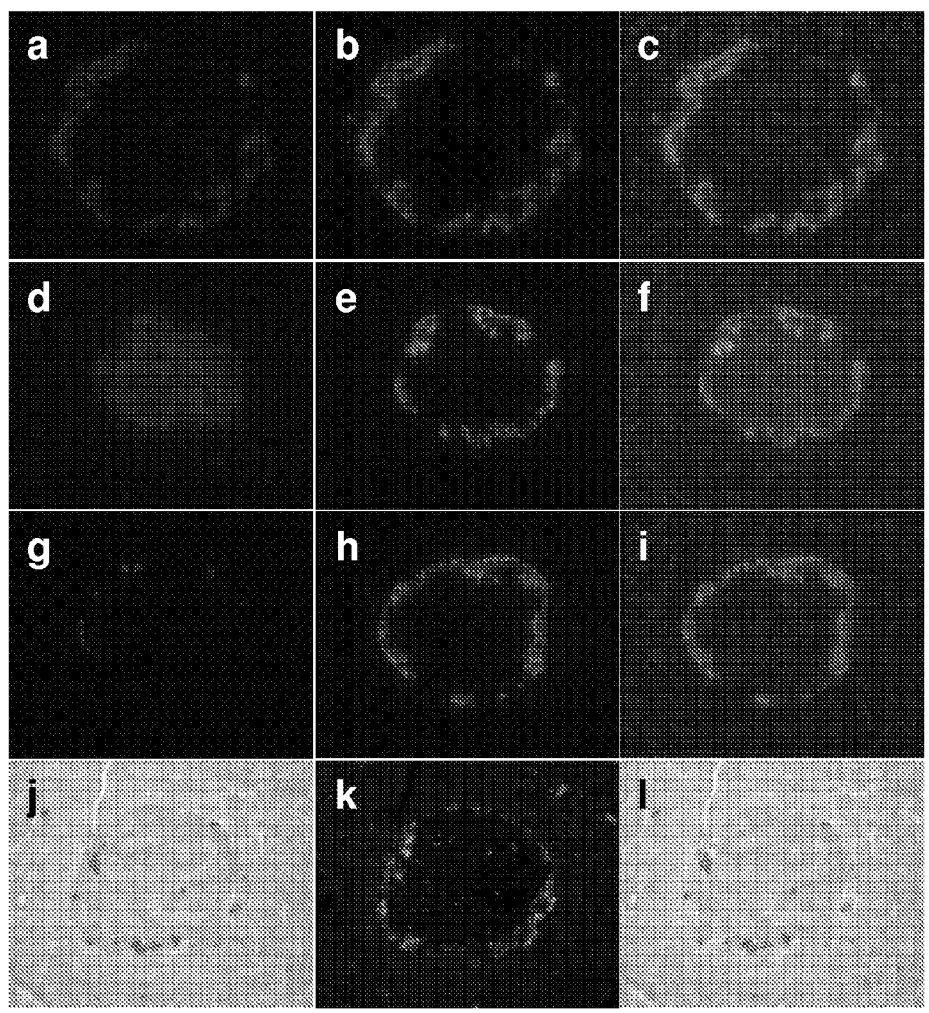
FIG. 2: Determination of IHoP in the normal rat pancreatic islets. (a-l) Double-immunofluorescence and immunohistochemical staining for glucagon (red; a), insulin (red; d), somatostatin (red; g) and pancreatic polypeptide (brown; j) with IHoP (green; b, e, h and k) on the normal rat pancreas counter-stained with nuclear DAPI (blue). The image in (c) represents a merged image from (a) and (b), (f) is from (d) and (e), (i) is (g) and (h), (l) is (j) and (k). Yellow signal indicated co-localization of both of proteins in the same cells (c). Original magnification is ×400. Data shown represent one of three experiments with similar results.

The inventors also examined IHoP protein expression in pancreatic islets using double immunofluorescent and immunohistochemical staining. Normal islets express four types of hormones: glucagon (FIG. 2*a*), insulin (FIG. 2*d*), somatostatin (FIG. 2*g*) and pancreatic polypeptide (FIG. 2*j*), and IHoP was found to be expressed as well (FIG. 2 *b, e, h* and *k*). The inventors expected IHoP to co-express with insulin, but immunostaining results on the islet showed that insulin, somatostatin, and pancreatic polypeptide did not co-localize with IHoP (FIG. 2*f, i* and *l*). However IHoP (FIG. 2 *b*) was shown to co-localize with the glucagon producing (FIG. 2*a*) α-cells (FIG. 2*c*), indicating that IHoP is a new protein expressed by the α-cells of the pancreatic islet of Langerhans.

Effect of IHoP on Cell Proliferation and Insulin Synthesis from INS-1 Cells

Figure 3:
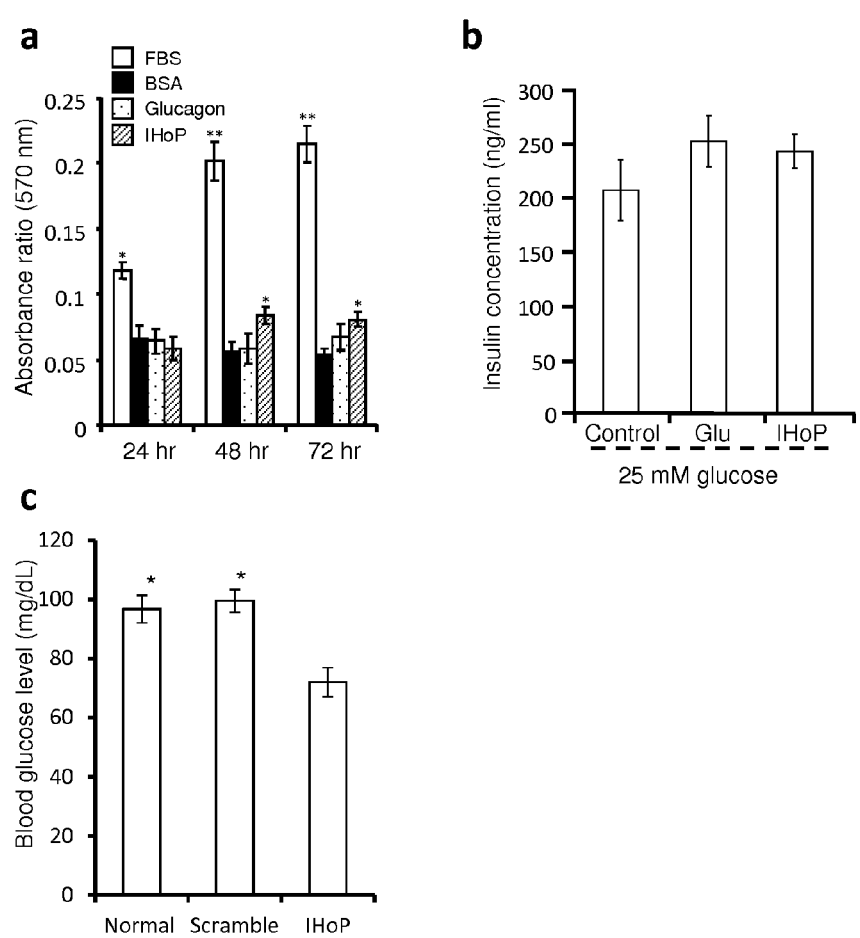
FIG. 3: Physiological test of IHoP function in insulin-producing INS-1 cells. (a) Effect of IHoP on INS-1 cell proliferation using MTT assay. The INS-1 cells were cultured with 10% FBS supplemented INS-1 culture medium (FBS; positive control), serum free INS-1 culture medium containing 0.5% BSA (BSA; negative control), 0.5% BSA with glucagon (1 μM) or IHoP (1 μM). The MTT assay was performed on cells cultured for 24, 48 and 72 hours. The data represents the mean±S.D. of five independent experiments. *$p<0.05$ and **$p<0.01$. (b) Determination of insulin secretion into media following treatment with glucagon and IHoP. ELISA analysis of insulin secretions measured following collection of cell culture-conditioned media. INS-1 cells cultured in high-glucose medium, with glucagon (1 μM) or IHoP (1 μM) for 2 hours. Data represent the mean±S.D. of four independent experiments. (c) Blood glucose level following treatment with IHoP-siRNA. Rats received 50 μg of scramble-siRNA (Scramble) or IHoP-siRNA (IHoP) each, and non-treated (Normal). The data represents the mean±S.D. of blood glucose levels. *$p<0.05$.

The results indicated that IHoP was expressed by α-cells. The inventors examined the role of IHoP in proliferation of β-cells and insulin synthesis. INS-1 cells were cultured in the presence of IHoP or glucagon. FIG. 3*a* shows the effect of IHoP on INS-1 cell proliferation as determined by MTT assay. When cultured with 10% FBS supplemented medium, INS-1 cell proliferation was significantly activated. When cultured with IHoP in 0.5% BSA medium, INS-1 cell proliferation was significantly increased as compared to either 0.5% BSA medium alone or with glucagon alone (FIG. 3*a*). Furthermore, the inventors tested the effect of glucose challenge in combination with glucagon or IHoP treatment on insulin synthesis. The glucose challenge with glucagon and IHoP treated groups demonstrated slightly enhanced secretion of insulin into the media as compared to 25 mM glucose medium alone (FIG. 3*b*). However the data was not significant. These results indicate that IHoP did not have a direct effect on insulin secretion; though, the peptide does appear to stimulate cellular proliferation.

Detection of Apoptosis Signal in the IHoP-siRNA Injected Pancreatic Islets

IHoP-siRNA was injected twice at two-week intervals, and then pancreatic tissue was harvested two weeks later. The inventors tested blood glucose levels in the animals receiving injections before and after sacrifice (FIG. 3*c*). Before injection of siRNA, the blood glucose levels shown were within the normal range, around 81-107 mg/dl (97.5±3.3 mg/dL). After siRNA treatments, IHoP-siRNA injected rats demonstrated significantly lower blood glucose levels 72±4.9 mg/dL (63-85 mg/dL), compared to either rats receiving scramble-siRNA and control group showed no change in blood glucose levels 99.5±4.66 mg/dL (82-111 mg/dL) and 96.7±3.85 mg/dL (81-117 mg/dL). These data indicate that IHoP might play a role in the regulation of blood glucose levels.

In addition to insulin secretion, the inventors determined both glucagon and IHoP expression in the IHoP-siRNA treated pancreas via immunohistochemistry. Normal pancreas expressed both glucagon (FIG. 4*a*) and IHoP (FIG. 4*b*). Treatment with scrambled-siRNA showed no effect on IHoP expression (FIG. 4*c*), nor any significant impact on other hormones such as insulin, glucagon, somatostatin and pancreatic polypeptide expression (data not shown). However, IHoP-siRNA treated rat pancreas showed a dramatic loss of IHoP expression (FIG. 4*e*), as well as loss of glucagon expression (FIG. 4*d*). IHoP-siRNA treatment did not affect the expression of insulin (FIG. 4*f*), somatostatin (FIG. 4*g*) or pancreatic polypeptide (FIG. 4*h*). The inventors next sought to determine if the loss of both IHoP and glucagon would affect the islet. The inventors first examined apoptosis in both siRNA and scrambled injected rats. The inventors saw a significant amount of apoptosis occurring in the islet, mainly within the insulin producing β-cells, but all islet cell types were effected to some degree (FIG. 4*i*), an atypical result that was not seen in the scrambled-siRNA injected islets (FIG. 4*j*). Together, these results indicate that IHoP appears mediate to suppression of glucagon synthesis from the α-cells in the pancreatic islets, as well as mediating activation of apoptosis signal in islets.

The inventors also examined expression of both glucagon and IHoP on the pancreatic tissues from NOD diabetes phenotype mice (FIG. 4*k* and *l*). In NOD/wild type mice, the pancreatic islets expressed glucagon (FIG. 4*k*) and IHoP (FIG. 5*l*), also infiltrated T-cells were stained by IHoP (FIG. 4*l*). These results indicate that IHoP may control of glucagon synthesis and apoptosis in the pancreatic islets.

Detection of IHoP in the Pancreatic Islet from Pre- and Post-Onset Type-1 Diabetic Patients Upon evaluation of IHoP expression in normal human pancreatic islets, double immunofluorescence staining showed co-localization of glucagon (FIG. 5a) and IHoP (FIG. 5b) on the α-cells within the islet (FIG. 5c). The inventors also determined expression of glucagon and IHoP in the pre- and post-onset diabetic patient's pancreatic tissues. Immunohistochemical staining of normal human pancreatic islets for glucagon (FIG. 5d) and IHoP (FIG. 5e) localized these proteins to the islet. Furthermore, the islets from pre-type-1 diabetic patients demonstrated stronger expression of glucagon (FIG. 5f and h), along with IHoP (FIG. 5g and i) as compared to normal islets. In the islets of post-onset-type-1 diabetic patients, glucagon was detected in the islets (FIG. 5j and l), but there was no expression of IHoP (FIG. 5k and m), suggesting that the absence of IHoP may be contributing, to the pathophysiological effects seen in these tissues. Moreover these results indicate that IHoP may represent a new target for treatment of diabetes mellitus.

Discussion

The findings set forth herein show that IHoP is a new functional protein in the pancreatic islet, functioning in a role of hormone synthesis for islet homeostasis. A previous report indicated that BM-derived IPCs cluster expressed the four major proteins of glucagon, insulin somatostatin and pancreatic polypeptide, found in the pancreatic Langerhans islet.[21] It was expected that IHoP expressed on the insulin-producing β-cells, however this protein co-localized with glucagon synthesizing α-cell. These results indicated that the IHoP is a new marker of α-cell and pancreatic islet.

The data presented here demonstrate that the control of glucagon synthesis in the α-cell of the pancreatic islet is regulated by IHoP. In vitro data indicate that IHoP has an effect on proliferation of insulin producing INS-1 cells. Furthermore, treatment of normal rats with IHoP-siRNA, resulted in suppression of glucagon synthesis, and subsequent loss of regulation of insulin synthesis from β-cells. Finally, IHoP suppression led to a break in homeostasis and induction of apoptosis in the pancreatic islet. In NOD/wild type mice, it was found that IHoP and glucagon were overexpressed in the pancreatic islet. Additionally, infiltrating T-cell expressed IHoP, but not glucagon. A similar expression pattern was seen in the human pre-type-1 diabetic islet. However, although the islets of post-onset-type-1-diabetics were positive for glucagon, there was no expression of IHoP. This may suggest that IHoP plays a critical role in the regulation of the islet homeostasis via mediating glucagon synthesis by α-cells.

Recent reports have identified several factors that directly regulate α-cell secretion of glucagon. For example, insulin is a potent inhibitor of islet glucagon release, and somatostatin and GLP-1 also inhibit glucagon secretion.[29,30] Glucose also suppresses glucagon secretion, but may do so indirectly through insulin or GABA.[31] During glucagon synthesis from the α-cells, proglucagon is controlled by cell-specific expression of prohormone convertase (PC) enzymes. An essential role for PC2 in the processing of islet proglucagon is revealed by studies of the PC2 knockout mouse. This mouse has a mild to low level of blood glucose, and elevated proinsulin, and exhibits a major defect in the processing of proglucagon, secreted by a typical secretory granule in the α-cell, to mature pancreatic glucagon.[32,33] Similarly, the data presented herein indicates that following IHoP knockdown, rat pancreatic islets showed suppression of glucagon synthesis from pancreatic α-cells resulted in an induction of insulin secretion by β-cells, resulting in decreased blood glucose level. These results indicate that IHoP may directly control glucagon synthesis by α-cells within the pancreatic islets.

Figure 4:
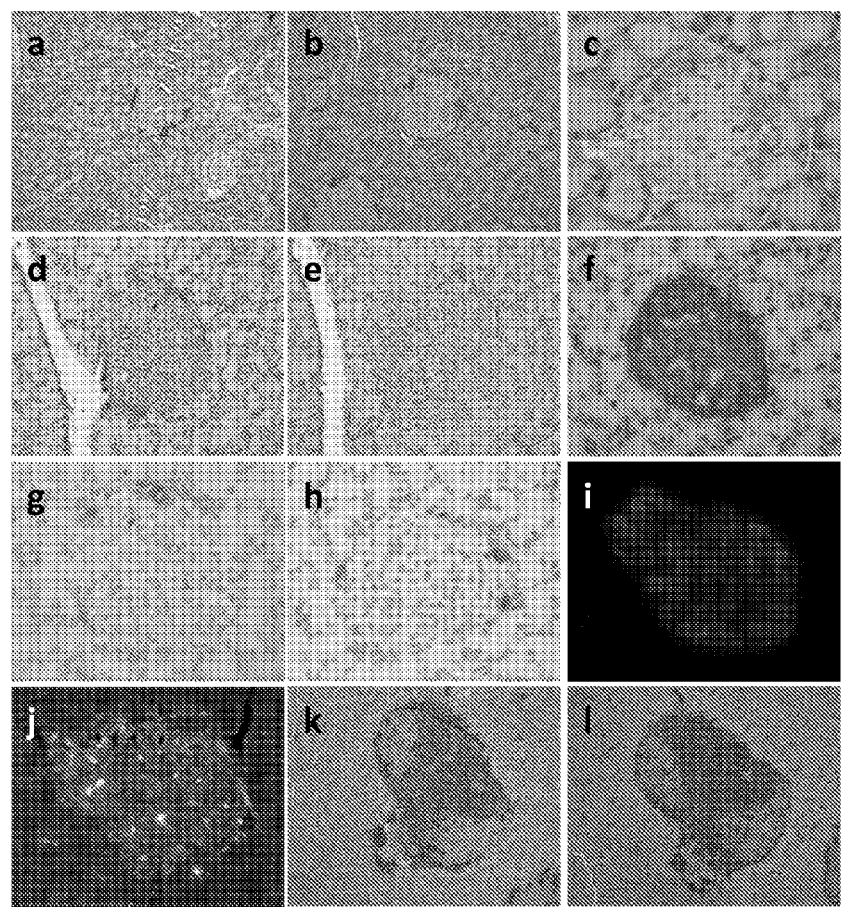
FIG. 4: Detection of apoptosis signal in the islets of IHoP knockdown rats and pattern of IHoP in NOD/wild type mice pancreatic islets. (a-e) Normal rat islets expressed glucagon (a; brown) and IHoP (b; brown). Islets transduced with scrambled-siRNA were positive for IHoP (c; brown). However, after transduction with IHoP-siRNA, IHoP was successfully inhibited (e; brown), also glucagon was suppressed (d; brown) in the islets. Original magnification of (a) to (e) is 200×. (f-h) IHoP knockdown did not affect expression of other islet specific hormones, such as insulin (f; brown), somatostatin (g; brown) and pancreatic polypeptide (h; brown). Original magnification of (f) to (h) is 400×. (i-j) Detection of apoptosis in the IHoP-siRNA treated pancreatic islet. Scrambled siRNA injected rat islets were stained by insulin (i; red) and did not express an apoptotic signal (green in nuclei) in β-cell of islet (insulin; red); or acinar area. However, suppression of IHoP led to detection of apoptosis (j; green) in islet. This was true for insulin-positive cells (j; red) as well as the other islet cells. (i) and (j) used dual-filters for detection of rear green signal in the nuclei. Original magnification of (i) and (j) is 200×. (k-l) The NOD diabetes phonotype mice islets were infiltrated by T-cells, and the islets were shown to express glucagon (k; brown). IHoP was expressed in the islet and in T-cell-rich areas (l; brown), while infiltrating T-cells within the islets stained IHoP. Original magnification of (k) and (l) is 200×. Data shown represent one of three experiments with similar results.
Figure 5:
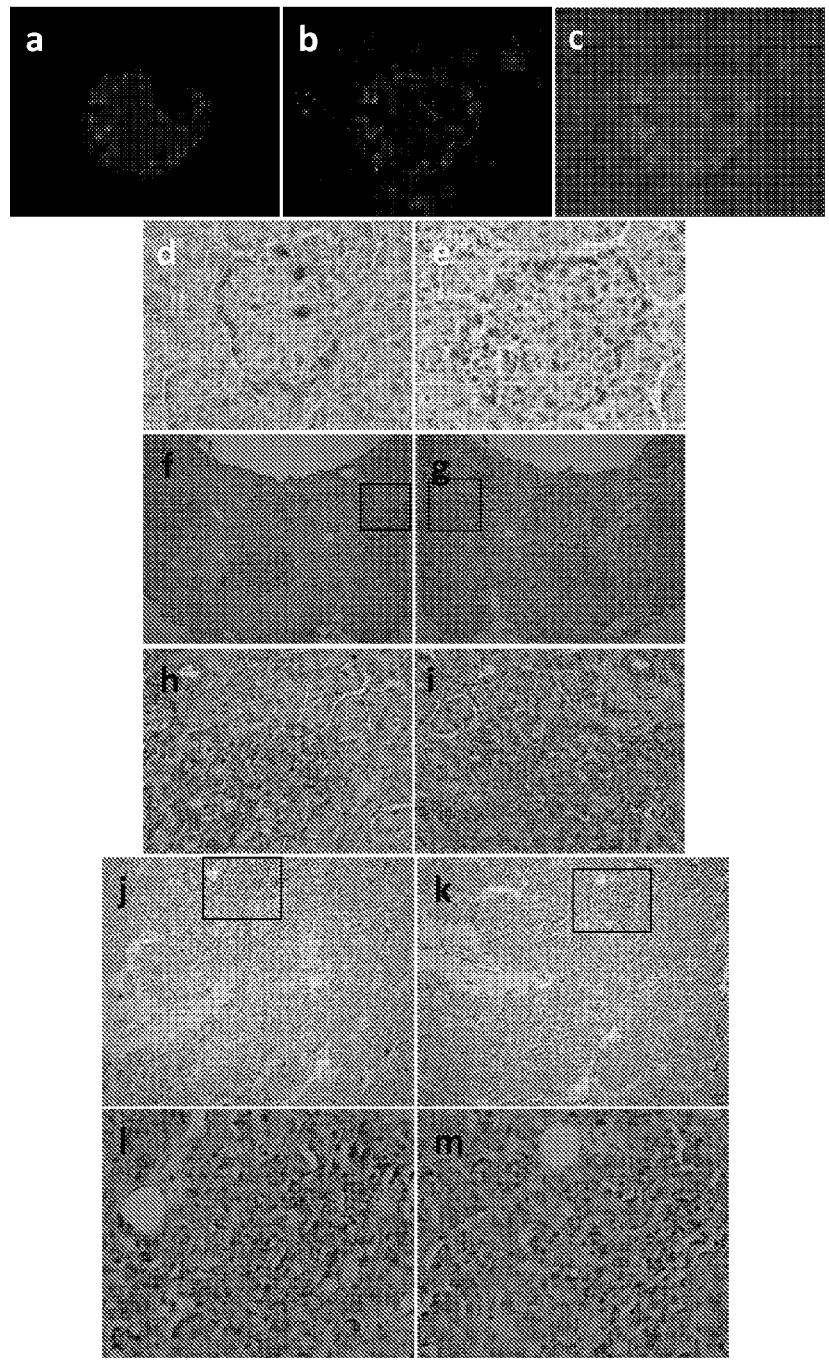
FIG. 5: Detection of IHoP in the pancreatic islets of pre- and post-onset type-1 diabetic patients. (a-f) Determination of IHoP in the human pancreatic tissues. Double-immunofluorescence staining for glucagon (a; red) with IHoP (b; green) in normal human pancreatic tissue counter-stained with nuclear DAPI (blue). (c) Merged image from (a) and (b) (c; yellow). Immunohistochemistry for glucagon (d; brown) and IHoP (e; brown) in the normal human pancreas. Original magnification is 400×. (f-m) Detection of glucagon and IHoP in the pancreatic islets of pre- and post-onset type-1 diabetic patients. Glucagon (f and h; brown) and IHoP (g and i; brown) were expressed in the pre-onset type-1 diabetic patient pancreatic islets. The post-onset type-1 diabetic pancreatic islets were positive for glucagon (j and l; brown), however IHoP was not detected in the islets (k and m). Original magnification of (f), (g), (j) and (k) is 100×, and (h), (i), (l) and (m) is 400×. The boxed areas in (f), (g), (i), (j) and (k) are shown in higher magnification in (h), (i), (l) and (m). Data shown represent one of three experiments with similar results.

Utilizing siRNA technology, the resulting data indicated that IHoP-siRNA suppressed both IHoP and glucagon (directly or indirectly) in the pancreatic islets. The β-cells will continuously produce and secrete insulin (FIG. 3c), leading to uncontrolled insulin secretion in these cells and subsequent apoptosis (FIG. 4). Type 1-diabetes is considered to be a chronic autoimmune disease in which insulin-producing β-cells are gradually destroyed by autoreactive T-cells. The autoimmune disease associated with type-1 diabetes is mediated through the major histocompatibility complex (MHC) class I molecules that is required for the negative selection of autoreactive T-cells.[34,35] Also Fas receptor activation has been demonstrated in pancreatic islet cells during the onset of type-1 diabetes.[36] However, contradictory evidence has been published suggesting that apoptosis is not a major mechanism of β-cell destruction in type-1 diabetes.[37] The data herein certainly favors the notion that apoptosis plays a role in type-1 diabetes, and that IHoP expression influences (directly or in directly) this process.

The following treatments of IHoP-siRNA, blood glucose levels were decreased. This is likely a result of the concurrent suppression of glucagon synthesis (FIG. 3c). It is possible that suppression of IHoP may lead to a inhibition of glucagon synthesis and subsequently increase β-cell function and proliferation. Generally, approximately 15-20% of cells in the islet expressed glucagon.[1] However, in the pre-type-1 diabetic pancreatic islets, glucagon seemed to be expressed in a majority of the cells comprising the islet (FIG. 5f),[8] and IHoP appeared to follow a similar pattern (FIG. 5g). However the post-onset-type-1 diabetic pancreatic islets showed a loss of IHoP but remained positive for glucagon. The loss of IHoP with continued glucagon output may be lead to activation of apoptosis in the islets, which then leads to decreased insulin synthesis and secretion. This may promote T-cell infiltration and removal of the abnormally functioning β-cells (FIG. 4k and l). These data indicate that IHoP may function to regulate glucagon synthesis and maintain a balance in the secretion of both glucagon and insulin from islets. Taken together, up- or down regulation of IHoP in the pancreatic islets appears to play an important role in maintaining islets homeostasis. However, the question still remains as to how the balance between IHoP and glucagon becomes dysregulated, and which factor(s) control the interaction of these hormones.

It is demonstrated herein that IHoP protein co-localizes with glucagon secreting α-cells in normal pancreas. Gene knockdown by siRNA technology has proven to be a reliable method for the determination of gene functionality; however it does not completely explain the mechanisms by which the gene acts in vivo. To this end, upon suppression of IHoP expression via induction of siRNA, the islet loses IHoP expression and glucagon suppression. Recent studies demonstrate of processing of glucagon release, the proglucagon in the α-cell remains under active investigation, current evidence supports an important role for PC2 in the process.[38-40] However whether or not PC2 directly cleaves proglucagon to glucagon remains unclear. The results herein indicate that IHoP positively regulates glucagon synthesis, and controls insulin secretion from β-cells. This suggests that IHoP may possess therapeutic potential as a counter-regulator of the hormones responsible for maintenance of blood glucose concentration.

Figure 6:
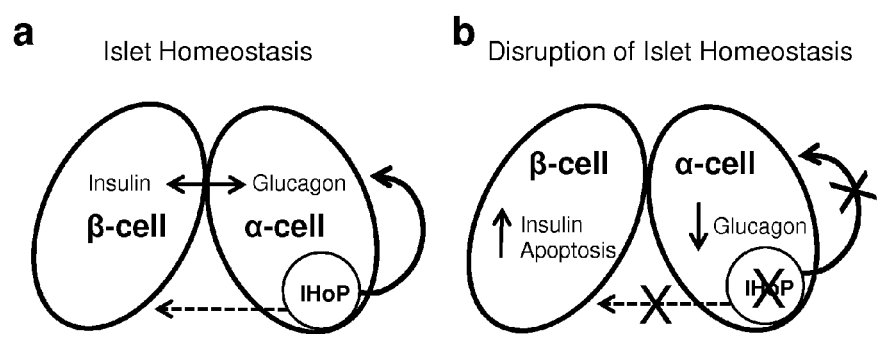
FIG. 6: Schematic diagram of possible IHoP function within the pancreatic islet. (a) Normal islet homeostasis. The dashed arrow is indicative of the effects of IHoP on β-cells. Whether these effects are direct or indirect has yet to be determined. (b) Inhibition of IHoP in islet results in several changes in the islet, including apoptosis in β-cells as well as a decrease in glucagon secretion in α-cells.

The present data focuses on the expression of IHoP within the pancreatic islets in relation to type-1 diabetes. In FIG. 6, a schematic representation of the findings on the function of IHoP in the pancreatic islet is presented. IHoP functions both to maintain homeostasis via the control of glucagon expression, as well as by regulating apoptosis in the islet.

The present disclosure presents a new functional protein (IHoP), and demonstrates that this protein co-localizes with glucagon expressing α-cells in the pancreatic islets. The role of IHoP in the islet appears to involve the regulation of hormone secretion as well as activation of apoptosis within the islets. However, the mechanism(s) by which IHoP regulates these processes (i.e. directly or indirectly) require further development and will require further studies. However, the results provided herein suggest that IHoP will prove to be a powerful tool for the study of pancreatic islet homeostasis, as well as offering a new target for the treatment of type-1 diabetes.

References

1. Elayat A A, el-Naggar M M, Tahir M. An immunocytochemical and morphometric study of the rat pancreatic islets. *J Anat.* 1995; 186:629-637.
2. Dunbar J C, Walsh M F. Glucagon and insulin secretion by dispersed islet cells: possible paracrine relationships. *Horm Res.* 1982; 16:257-267.
3. Fujimoto W Y, Kawazu S, Ikeuchi M, et al. In vitro paracrine regulation of islet B-cell function by A and D cells. *Life Sci.* 1983; 32:1873-1878.
4. Stephen L A, Kathy B, Barb S, et al. Glucose Metabolism and Regulation: Beyond Insulin and Glucagon. *Diabetes Spec.* 2004; 17:183-190.
5. Webb G C, Akbar M S, Zhao C, et al. Glucagon replacement via micro-osmotic pump corrects hypoglycemia and alpha-cell hyperplasia in prohormone convertase 2 knockout mice. *Diabetes.* 2002; 51:398-405.
6. Gerich J E, Langlois M, Noacco C, et al. Lack of glucagon response to hypoglycemia in diabetes: evidence for an intrinsic pancreatic alpha cell defect. *Science.* 1973; 182:171-173.
7. Bolli G, de Feo P, Compagnucci P, et al. Abnormal glucose counterregulation in insulin-dependent diabetes mellitus: interaction of anti-insulin antibodies and impaired glucagon and epinephrine secretion. *Diabetes.* 1983; 32:134-141.
8. Gepts W. Pathologic anatomy of the pancreas in juvenile diabetes mellitus. *Diabetes.* 1965; 14:619-633.
9. Unger R H. Glucagon physiology and pathophysiology in the light of new advances. *Diabetologia.* 1985; 28:574-578.
10. Skyler J S, Krischer J P, Wolfsdorf J, et al. Effects of oral insulin in relatives of patients with type 1 diabetes: The Diabetes Prevention Trial-Type 1. *Diabetes Care.* 2005; 28:1068-1076.
11. Agardh C D, Cilio C M, Lethagen A, et al. Clinical evidence for the safety of GAD65 immunomodulation in adult-onset autoimmune diabetes. *J Diabetes Com.* 2005; 19:238-246.
12. Raz I, Elias D, Avron A, et al. Beta-cell function in new-onset type 1 diabetes and immunomodulation with a heat-shock protein peptide (DiaPep277): a randomised, double-blind, phase II trial. *Lancet.* 2001; 358: 1749-1753.
13. Keymeulen B, Vandemeulebroucke E, Ziegler A G, et al. Insulin needs after CD3-antibody therapy in new-onset type 1 diabetes. *N Engl J Med.* 2005; 352: 2598-2608.
14. Allison A C, Eugui E M. Mycophenolate mofetil and its mechanisms of action. *Immunopharmacology.* 2000; 47:85-118.
15. Vincenti F, Kirkman R, Light S, et al. Interleukin-2-receptor blockade with daclizumab to prevent acute rejection in renal transplantation. *N Engl J Med.* 1998; 338:161-165.
16. Hu C Y, Rodriguez-Pinto D, Du W, et al. Treatment with CD20-specific antibody prevents and reverses autoimmune diabetes in mice. *J Clin Invest.* 2007; 117:3857-3867.
17. Weissman I L. Translating stem and progenitor cell biology to the clinic: barriers and opportunities. *Science.* 2000; 287:1442-1446.
18. Shapiro A M J, Lakey J R T, Ryan E A, et al. Islet transplantation in seven patients with type 1 diabetes mellitus using a glucocorticoid-free immunosuppressive regimen. *N Engl J Med.* 2000; 4:230-238.
19. Ramiya V K, Maraist M, Arfors K E, et al. Reversal of insulin-dependent diabetes using islets generated in vitro from pancreatic stem cells. *Nat Med.* 2000; 6:278-282.
20. Lumelsky N, Blondel O, Laeng P, et al. Differentiation of embryonic stem cells to insulin-secreting structures similar to pancreatic islets. *Science.* 2001; 292:1389-1394.
21. Oh S H, Muzzonigro T M, Bae S H, et al. Adult bone marrow-derived cells trans-differentiating into insulin-producing cells for the treatment of type I diabetes. *Lab Invest.* 2004; 84:607-617.
22. Oh S H, Witek R P, Bae S H, et al. Detection of transketolase in bone marrow-derived insulin producing cells: Benfotiamine enhances insulin synthesis and glucose metabolism. *Stem Cell & Dev.* 2008; 18:37-45.
23. The RIKEN Genome Exploration Research Group Phase II Team and FANTOM Consortium. Functional annotation of a full-length mouse cDNA collection. *Nature.* 2001; 409: 685-690.
24. Gotoh M., Maki T, Kiyoizumi T, et al. An improved method for isolation of mouse pancreatic islets. *Transplantation.* 1985; 40:437-438.
25. Elbashir S M, Harborth J, Lendeckel W, et al. Duplexes of 21-nucleotide RNAs mediate RNA interference in cultured mammalian cells. *Nature.* 2001; 411:494-498.
26. Yu J Y, DeRuiter S L, Turner D L. RNA interference by expression of short-interfering RNAs and hairpin RNAs in mammalian cells. *Proc Natl Acad Sci USA.* 2001; 99:6047-6052.
27. Brummelkamp T R, Bernards R, Agami R. A system for stable expression of short interfering RNAs in mammalian cells. *Science.* 2002; 296:550-553.
28. Mosmann T. Rapid colorimetric assay for cellular growth and survival: application to proliferation and cytotoxicity assays. *J Immunol Methods.* 1983; 65:55-63.
29. Shi Z Q, Rastogi K S, Lekas M, et al. Glucagon response to hypoglycemia is improved by insulin-independent restoration of normoglycemia in diabetic rats. *Endocrinology.* 1996; 137:3193-3199.
30. Dumonteil E, Magnan C, Ritz-Laser B, et al. Insulin, but not glucose lowering corrects the hyperglucagonemia and increased proglucagon messenger ribonucleic acid levels observed in insulinopenic diabetes. *Endocrinology.* 1988; 139:4540-4546.
31. Rorsman P, Berggren P O, Bokvist K, et al. Glucose-inhibition of glucagon secretion involves activation of GABAA-receptor chloride channels. Nature 1989; 341: 233-236.
32. Furuta M, Carroll R, Martin S, et al. Incomplete processing of proinsulin to insulin accompanied by elevation of Des-31,32 proinsulin intermediates in islets of mice lacking active PC2. *J Biol Chem.* 1988; 273:3431-3437.
33. Furuta M, Zhou A, Webb G, et al. Severe defect in proglucagon processing in islet A-cells of prohormone convertase 2 null mice. *J Biol Chem.* 2001; 276:27197-27202.
34. Faustman D, Li X P, Lin H Y, et al. Linkage of faulty major histocompatibility complex class I to autoimmune diabetes. *Science.* 1991; 254:1756-1761.
35. Yan G, Fu Y, Faustman D L. Reduced expression of Tap1 and Lmp2 antigen-processing genes in the non-obese diabetic (NOD) mouse due to a mutation in their shared bidirectional promoter. *J Immunol.* 1997; 159: 3068-3080.
36. Chervonsky A V, Wang Y, Wong F S, et al. The role of Fas in autoimmune diabetes. *Cell.* 1997; 89:17-24.
37. Kang S M, Schneider D B, Lin Z, et al. Fas ligand expression in islets of Langerhans does not confer immune privilege and instead targets them for rapid destruction. *Nat Med.* 1997; 3:738-743.
38. Rouille Y, Westermark G, Martin S K, et al. Proglucagon is processed to glucagon by prohormone convertase PC2 in alpha TC1-6 cells. *Proc Natl Acad Sci USA.* 1994; 91:3242-3246.
39. Rothenberg M E, Eilertson C D, Klein K, et al. Processing of mouse proglucagone by recombinant prohormone convertase 1 and immunopurified prohormone convertase 2 in vitro. *J Biol Chem.* 1995; 270:10136-10146.
40. Rothenberg M E, Eilertson C D, Klein K, et al. Evidence for redundancy in propeptide/prohormone convertase activities in processing proglucagon: an antisense study. *Mol Endocrinol.* 1996; 10:331-341.

Example 2

Detection of IHoP Gene Expression

Figure 9:
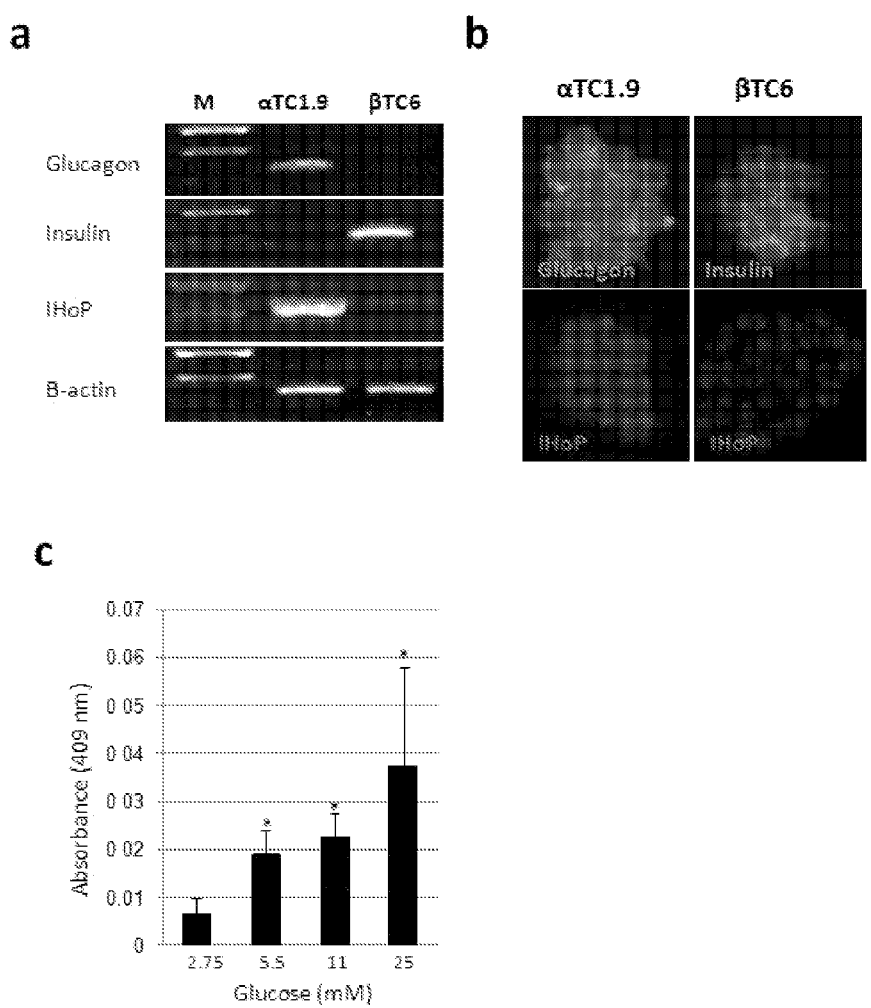
FIG. 9. Detection of IHoP gene and induction of IHoP secretion from the glucagon synthesizing α-cells. a, RT-PCR analysis for expression of IHoP gene in αTC1.9 and βTC6 cells. β-actin was used as an internal control. M indicates 100 bp ladder. b, Detection of IHoP protein on αTC1.9 and βTC6 cells. αTC1.9 cell expressed glucagon (green), βTC6 cells expressed insulin (green). Only αTC1.9 cells expressed IHoP (red). Counter-stain for nuclei was done with DAPI (blue). Original magnification is 200×. c, Induction of IHoP secretion into media. The αTC1.9 cells cultured in 0.5% BSA-DMEM supplemented with dose-dependent (2.75-25 mM) glucose conditions for 4 hours. ELISA assay for IHoP (c) in conditioned media from αTC1.9 cells. Data represent the mean±S.D. of five independent experiments. *$p<0.05$.

IHoP gene expression was carried out using αTC1.9 cell line (23). IHoP expression was confirmed by RT-PCR in mouse-derived glucagon-synthesizing αTC1.9 or insulin-secreting βTC6 (FIG. 9a). The αTC1.9 cells expressed glucagon and IHoP, while the βTC6 cells only expressed insulin (FIG. 9a). In addition, immunohistochemistry (24) revealed that only the αTC1.9 cells expressed the IHoP protein (FIG. 9b). These results confirm that IHoP expression as within the glucagon positive α-cells. Next, the secretion of IHoP into media under glucose challenge was tested. It was surmised that low glucose induced secretion of glucagon from the α-cells (13-15). However, when the αTC1.9 cells were cultured under high glucose conditions (25 mM), IHoP was secreted into media, but low glucose (2.5 mM) condition did not stimulated to secretion of IHoP (FIG. 9c). These results demonstrate that secretion of IHoP from the α-cells is differentially regulated in response to glucose concentrations.

Detection of Major Histocompatibility Complex II in Post Onset-NOD Mice Islet.

Figure 10:
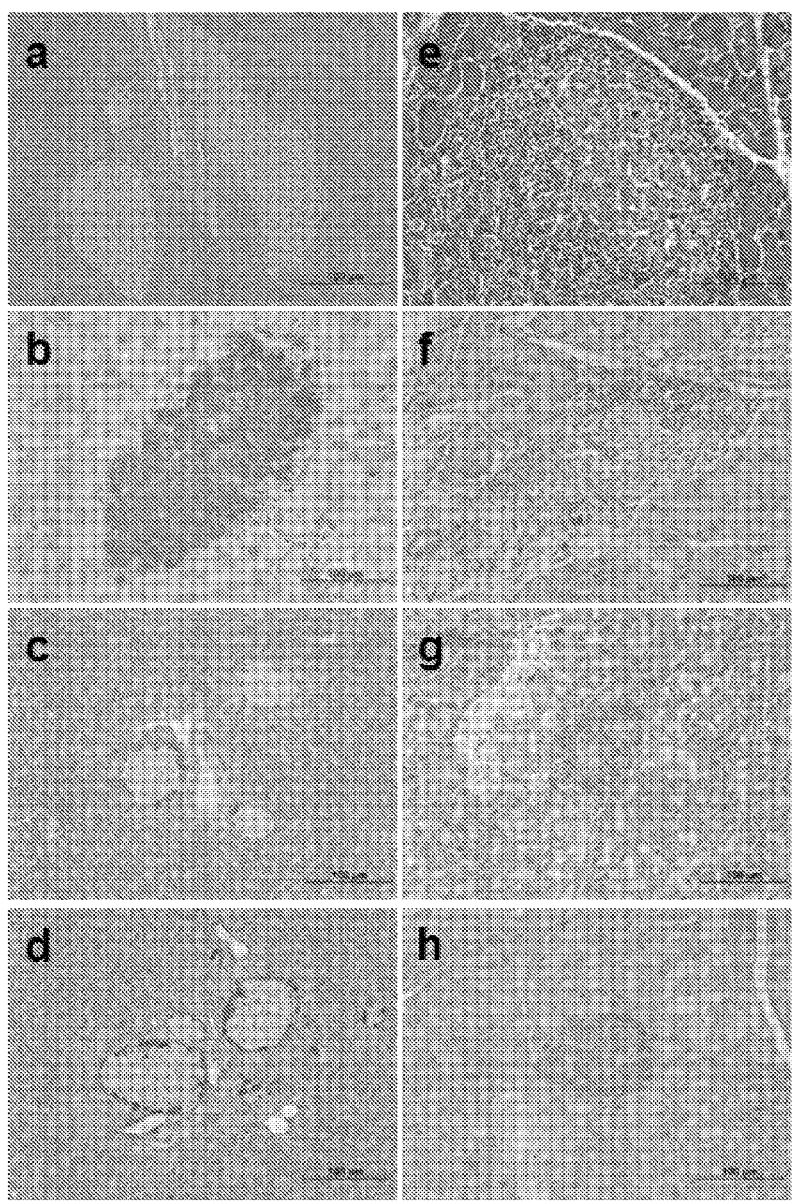
FIG. 10. Characterization of hormones expressed on the pancreatic islet. a, Normal mice islets showed absence of infiltrated T-cells, and more than 80% cells stained positive for insulin (brown; b), glucagon (brown; c) and IHoP (brown; d) expressed outside of islet. However, T-cells infiltrate into islets of post-onset NOD mice as seen H&E staining (e). Also, the islet lose insulin expression (brown; f), over express glucagon (brown; g) and IHoP (brown; h).

The non-diabetic pancreatic islet contains non-activated T-cells (FIG. 10a) and shows expression of insulin (FIG. 10c); approximately 10-15% of cells within the islet expressed glucagon (FIG. 10e) and IHoP (FIG. 10g). However, a post-onset NOD mice pancreatic islet contains activated T-cells (FIG. 10b), loss of insulin expression (FIG. 10d), and more than 50% of the islet cells stained positive for glucagon (FIG. 10f) and IHoP (FIG. 10h), which is completely different from what is seen in normal islets (FIG. 10c, e and g).

Figure 11:
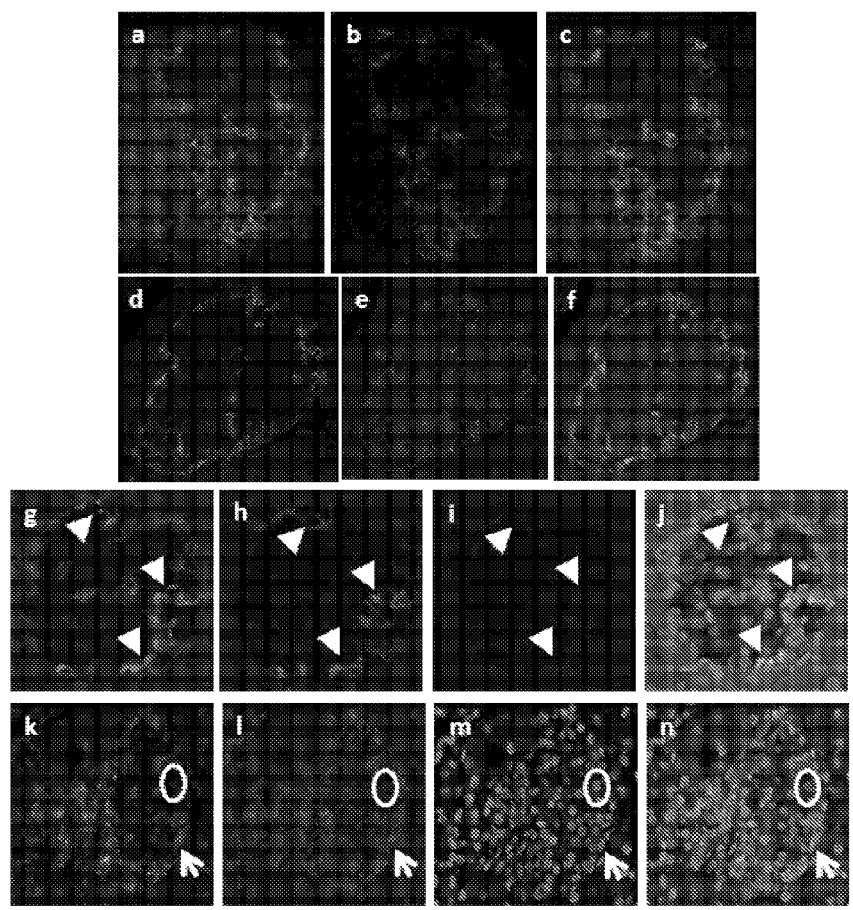
FIG. 11. Co-localiztion of IHoP or glucagon with MHC Class II in the islets. Double immunoflorescence staining of IHoP (green; a) and MHC Class II (red; b) on the post-onset NOD mice. c is the merged image from IHoP a and b (yellow). Double immuno-stained glucagon (green; d) with MHC Class II (red; e). f is the merged image from IHoP d and e (yellow). g, Triple immune-staining, IHoP (green; g), MHC Class II (red; h) and glucagon (blue; i). j is the merged image from g, h and i. The white arrow head indicates that IHoP, MHC Class II and glucagon were co-localized on the same cells. Also, glucagon (green; k), MHC Class II (red; l) and insulin (blue; m). The counter-stained with nuclear DAPI (blue; k and l). n is the merged image from k, l and m. The white color on the nuclear in the j, m and n was depolarization of unclear stained blue color. An arrow in the k to n was indicated that co-stained MHC Class II (l) and insulin (m) without glucagon (k). A circle indicates that insulin positive cell (m) did not co-stain with glucagon (k) and MHC Class II (l). Original magnification is 400×.

Characterizing cell types via double immunostaining was conducted. Cell expressing IHoP (FIG. 11a) were co-localized with MHC Class II (FIG. 11b and c), and glucagon-synthesizing cells (FIG. 11d) also expressed MHC Class II (FIG. 11e and f). IHoP, MHC Class II and glucagon on the NOD mice pancreatic islet was also tested. IHoP (FIG. 11g), MHC Class II (FIG. 11h) and Glucagon (FIG. 11i) were co-localized (FIG. 11j). Furthermore, glucagon (FIG. 11k) and MHC Class II (FIG. 11l) co-localized on the islet cells, also insulin positive cells (FIG. 11m) were detected in the islet. Many of insulin-positive cells (FIG. 11m) did not co-stain with MHC Class II (FIG. 11n). These results suggest a possible interaction between islet α-cells and T-cells during the development of T1 D in NOD mice.

Prevention of Hyperglycemia by Suppression of IHoP

Figure 12:
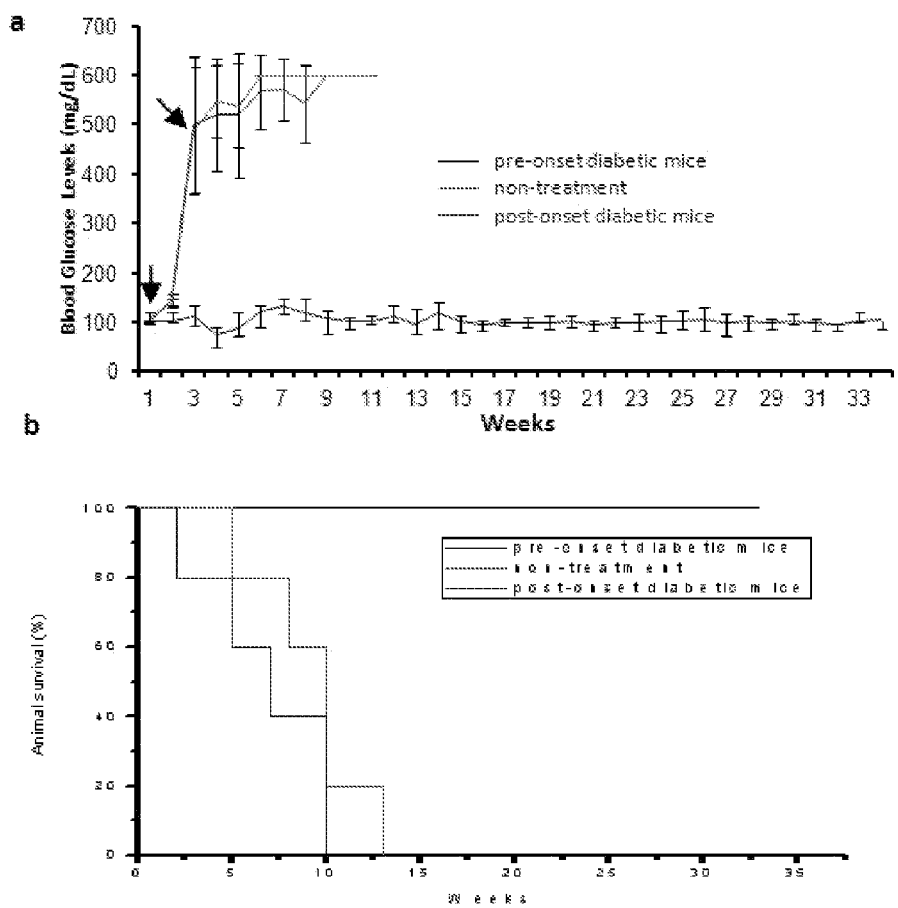
FIG. 12. Prevention of hyperglycemia in IHoP-siRNA treated pre-onset NOD mice. a, Blood glucose levels of IHoP-siRNA treated NOD mice. Subsequently the changes of blood glucose levels were evaluated. Red solid line indicates non-treatment group, which only received injections of carrier, black solid line indicates IHoP-siRNA received pre-onset (blood glucose levels were 100-150 mg/dL) group and blue solid line indicates IHoP-siRNA injected into post-onset (more than 300 mg/dL glucose levels) group. b, Survival rate in IHoP-siRNA treated pre- or post-onset NOD mice. The IHoP-siRNA treated pre-onset NOD mice (black solid line) never saw an increase in their blood glucose levels and 100% survived. However, nontreated mice (red solid line) and post-onset diabetic NOD mice (blue solid line) became hyperglycemic and died.

Next, the role of IHoP in the development of T1D in NOD mice (25) was tested. Under experiments conducted, NOD/ShiLtj mice were characterized by insulitis, a leukocytic infiltrate of the pancreatic islets. NOD mice were divided into two categories based on blood glucose levels, pre-onset (100-150 mg/dl) group, and post-onset (over 300 mg/dl) group. Both the pre- or post-onset NOD mice received IHoP-siRNA, at the appropriate respective ages with plasma glucose levels measured during the 33-weeks experimental period (FIG. 12a). The IHoP-siRNA injected pre-onset mice demonstrated lower blood glucose levels (73±6.69 mg/dL) as compared to normal mice (91±7.62 mg/dL). However, glucose levels in post-onset mice were not affected until the mice succumbed to the extreme hyperglycemia. In addition the pre-onset NOD mice receiving IHoP-siRNA demonstrated a high survival ratio until the end of experiments. Comparatively, non-treated mice as well as post-onset mice that received IHoP-siRNA showed a much lower survival rate with animals only surviving out to about 13 weeks (FIG. 12b). These results clearly indicate that suppression of IHoP expression during the onset of T1 D in NOD mice prevent the autoimmune destruction of insulin producing β-cells, and block the development of T1 D.

IHoP Plays a Role in Islet Homeostasis and Protection of Insulin Producing β-Cells.

Figure 13:
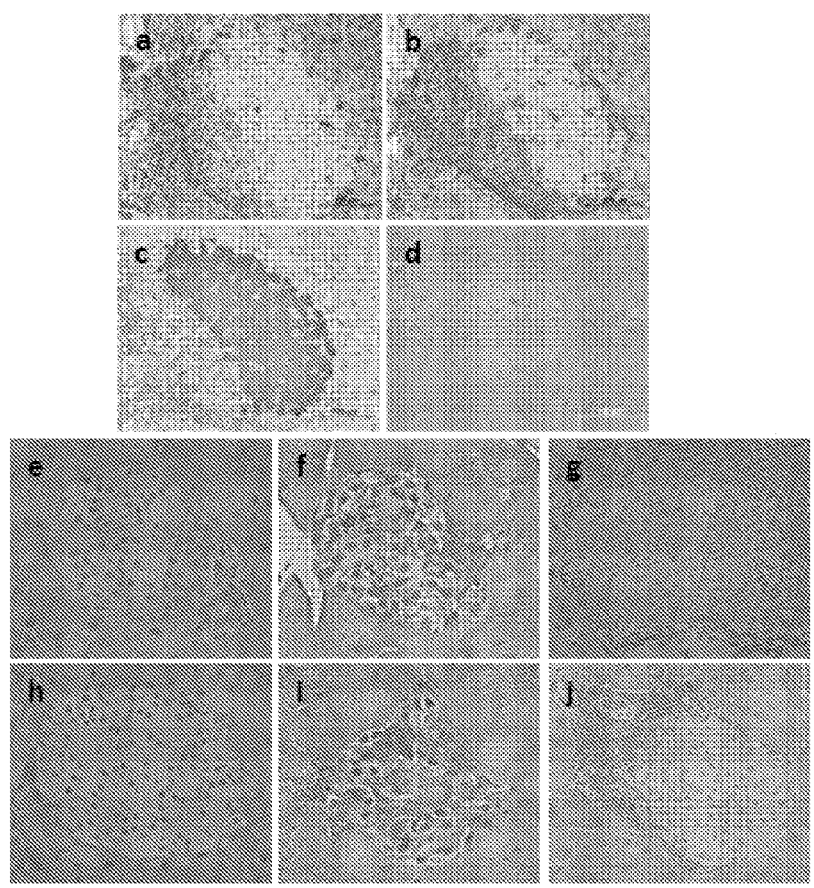
FIG. 13. Suppression of MHC Class II in IHoP-siRNA treated pre-onset NOD mice islets. IHoP-siRNA treated pre-onset NOD mice islets showed far less expression of glucagon (a) and IHoP (b) but expressed insulin (c) in the islet. The IHoP-siRNA treated pre-onset NOD mice vary rarely stained positive for MHC Class II in the islet (d). Also, normal mice islets were negative for CD 80 (e) and CD 86 (h). However post on-set NOD mice islets were positive for CD 80 (brown; f) and CD 86 (brown; i). Dramatically, very few numbers of islet cells were stained by CD 80 (g) and CD 86 (j). Original magnification is 200×.

Immunohisotchemical analysis showed that the non-treated pancreatic islets were not positive for insulin (FIG. 10f), but were however positive for glucagon (FIG. 10g) and IHoP (FIG. 10h). On the other hand, pre- or post-onset NOD mice receiving IHoP-siRNA showed the opposite pattern in comparison; the islets contained a normal number of glucagon-positive cells (FIG. 13a) and IHoP-positive cells (FIG. 13b), as well as a normal number of insulin positive cells (FIG. 13c). Although there are T-cells present around the islets, there are no signs of infiltration and it appears that the islet has returned to a normal state (FIG. 13c, f, i and l). These data indicate that inhibition of IHoP during the pre-onset stage allows the islet to return to a normal state with T cell infiltration being abated.

Expression of MHC Class II in the islets of post-onset diabetic or IHoP-siRNA-treated mice was examined. Normal mice did not express MHC class II on the islets (FIG. 13d), however non-treated NOD mice were positive for MHC Class II on the islet (FIG. 13e). However, pre-onset NOD mice receiving IHoP-siRNA very rarely expressed MHC Class II (FIG. 13f). We also looked downstream of MHC II, examining CD 80 and CD 86 on the experimental islets. Normal pancreatic islet did not express CD80 (FIG. 13g) and CD86 (FIG. 13j). The post-onset NOD mice were positive for CD 80 (FIG. 13h) and CD 86 (FIG. 13k) on the islet. However, IHoP-siRNA treated NOD mice did not express either antigen CD80 (FIG. 13i) or CD86 (FIG. 13l). This indicates that the components required for T-cell activation are present in NOD mice, but not if IHoP-siRNA is administered prior to the onset of T1D.

Discussion

The present Example reveals a new therapeutic target for the prevention of T1D. The data presented here within demonstrates that IHoP regulates the production of glucagon by α-cells. Glucose levels control insulin expression and secretion into the blood stream. However, hyperglycemia causes a decrease in the rate of insulin synthesis, suppression of glucokinase expression, decreased mitochondrial function, compromised exocytotic mechanisms, and accelerated apoptosis (27-29). Secretion of IHoP by α-cells under high glucose conditions confers resistance to apoptosis within the β-cell population. Based upon these findings it appears that IHoP may also be able to control certain β-cells functions under high glucose conditions.

Generally, approximately 15-20% of cells in the islet express glucagon (30), however in the pre-T1D pancreatic islets, glucagon was expressed by a majority of the cells comprising the islet (FIG. 10g) (13). The expression of glucagon, IHoP, insulin and islet number in pancreatic islets was evaluated, making a comparison between normal mice, post-onset diabetic mice, and either pre- (pre-IHoP-siRNA) or post-onset NOD mice (post-IHoP-siRNA) receiving IHoP-siRNA. In the subject experiments, the normal pancreas shows approximately 13.2±5.9 islets/slide were insulin positive, while a small number (2.8±4.9 islets/slide) exist in the post-onset pancreatic islet. However, the pre-IHoP-siRNA pancreas has a similar number (15±7.7 islets/slide) to normal pancreas. The pattern of glucagon expression in post-IHoP-siRNA treated mice show only 27.6% islet was normal pattern of glucagon. However, pre-IHoP-siRNA treated mice have 62.2% of the islets with a normal pattern. About IHoP expression, more than 71% of islet have shown abnormal expression in post-IHoP-siRNA, but pre-IHoP-siRNA mice shows only 4.7% abnormal pattern. In a comparison of T-cell activation, post-onset pancreatic islet shows 100% T-cell infiltration into the islet (FIG. 12e), however, in mice receiving IHoP-siRNA about 63% of islets are surrounded by T-cells, but have not infiltrated into islet (data not shown). This indicates that, at the cellular level, development of T1D may be completely avoided by suppressing IHoP expression. Taken together, the question still remains as to how the balance between IHoP and glucagon becomes dysregulated, and which factor(s) control the interaction of these hormones.

In the pre-IHoP-siRNA, the pancreas of those animals shows what appears to be normal expression of insulin and glucagon by their respective cell type. Also, those mice never developed into hyperglycemia and survived until finished experiments periods (33 weeks). However, not everything returned to normal, there was not a complete inactivation of T-cells. T-cells appeared to become activated and surrounded the islets, but did not infiltrate into the islets. This was not the case in post-onset NOD mice receiving IHoP-siRNA. The islet from the post-onset treated mice showed the β-cells were destroyed by autoimmune cells, as well as the continued expression of MHC Class II. When IHoP-siRNA was given during pre-onset of T1D the animals reverted to a normal state of euglycemia with normal islet morphology and histology. Normally, pancreatic endocrine cells do not express Class II major histocompatibility complex (MHC) molecules and the only weakly express Class I MHC (26). MHC Class II antigen has been shown to be aberrantly expressed in the pancreas in T1D (31-36). It was found that expression of MHC Class II, CD 80 and CD 86 on the pancreatic islets of NOD mice (FIG. 3 and FIG. 5), but did not detect any expression upon the treatment with IHoP-siRNA in pre-onset NOD mice. MHC Class II positive cells were co-localized with glucagon or IHoP expressing cells. Inhibition of the IHoP gene revealed that MHC Class II expression was eliminated within the islet. Interestingly, the aberrant expression of class II MHC was only observed in islets, which also had hyper-expression of class I MHC, and insulitis was only observed in approximately half of the islets having evidence of aberrant Class II MHC expression (34, 35). The abnormal expression of class II MHC appears to be focal in nature within any given islet and is restricted to a minority of insulin-containing β-cell (35, 36). This indicates that there is a critical point between the pre and post-onset stages of T1D that needs to be identified, and which could lead to an earlier diagnosis for the diabetic patient. This is further evidenced by the prevention of development to hyperglycemia as well as the protection of insulin-producing β-cells from infiltrated T-cells seen during the process of islet homeostasis and regulated by protein such as IHoP.

References And Notes

1. W. Gepts, *Acta Endocrinol Suppl (Coenh)* 205, 95 (1976).
2. J. S Skyler, et al., *Diabetes Care* 28, 1068 (2005).
3. C. D. Agardh, et al., *J. Diabetes Complication* 19, 238 (2005).
4. I. Raz, et al., *Lancet* 358, 1749 (2001).
5. B. Keymeulen, et al., *N. Engl. J. Med.* 352, 2598 (2005).
6. A. C. Allison, and E. M, *Immunopharmacology* 47, 85 (2000).
7. F. Vincenti, et al., *N. Engl. J. Med.* 338, 161-165 (1998).
8. C. Y. Hu, et al., *J. Clin. Invest.* 117, 3857 (2007).
9. Y. Guz, et al., *Endocrinology* 142:4956 (2001).
10. A. M. Shapiro, et al., *N. Engl. J. Med.* 343:230 (2000).
11. S H. Oh, et al., *Lab. Invest.* 84:607 (2004).
12. S H. Oh, et al., *Stem Cell & Dev.* 18, 37 (2009).
13. W. Gepts, *Diabetes* 14, 619-633 (1965).
14. A. K. Foulis, et al., *Diabetologia* 29, 267 (1986).
15. W. Gepts, and J. De Mey, *Diabetes* 27, 251 (1978).
16. S H. Oh, et al., *Pancreas* 41:22 (2012).
17. J. E. Gerich, et al *Science* 182, 171 (1973).
18. G. Bolli, et al., *Diabetes* 32, 134 (1983).
19. Z. Q. Shi, et al., *Endocrinology* 137:3193 (1996).
20. E. Dumonteil, et al., *Endocrinology* 139, 4540 (1998).
21. P. Rorsman, et al., *Nature* 341, 233 (1989).
22. R. H. Unge, *Diabetologia.* 28, 574 (1985).
23. The cell lines, glucagon synthesizing αTC1.9 and insulin producing βTC1 cells were kind gifts from Dr. Michael S. Lan (LSUHSC and the Research Institute for Children, Children's Hospital, New Orleans). RT-PCR was used for the detection of insulin, glucagon, IHoP, and β-actin genes by a previously described method (16). IHoP protein was detected by immunoflurescence staining in cells cultured on the chamber slide (Nalge Nunc International, Rochester, N.Y.). ELISA was performed on the conditioned media to analyze glucagon or IHoP secretion under glucose challenge using the direct ELISA protocol. All data shown represent one of at least three experiments with similar results. Values are expressed as the mean±SD. Statistical differences were analyzed using Student's t-test. P values of <0.05 were considered to denote statistical significance.
24. The following antibodies were used in this procedure: Rabbit anti-insulin (Santa Cruz Biotechnology, Inc., Santa Cruz, Calif.), Goat anti-glucagon (Santa Cruz), Rabbit anti-glucagon (Dako, Carpinteria, Calif.), anti-pancreatic polypeptide (Dako), goat anti-somatostatin (Santa Cruz), mouse anti-MHC-II (Novus Biologicals, Littleton, Colo.), rabbit anti-CD80 (Novus Bio.), Rabbit anti-CD86 (Abcam, Cambridge, Mass.) and rabbit anti-IHoP (prepared by GenScript Corp Piscataway, N.J.). Alexa Fluor 360, 488 or 568 donkey anti-rabbit and Alexa Flour 488 or 568 donkey anti-goat IgG (1:500, Invitrogen) were used as secondary antibodies, respectively. Nuclei were identified by DAPI (Vector Lab. Burlingame, Calif.). Detection of labeled cells was performed using Vector ABC kit (Vector Lab.) and 3,3'-diaminobenzidine tetrahydrochloreide (DAB) reagent (Dako). The counter staining was performed using Hematoxylin.

25. All procedures involving animals were conducted according to institutionally approved protocols and guidelines. Female NOD mice (8 weeks) were purchased from the Jackson Laboratory (Bar Harbor, Me.) and housed in specific pathogen-free facilities. Monitoring of blood glucose levels in the female NOD mice began at 10 weeks of age. The preparation and injection of IHoP-siRNA was performed following previously described methods (16). Before IHoP-siRNA injection, blood glucose levels were tested in all mice. The NOD mice were divided into 3 groups (n=5): one group was a non-treated control, while another group was injected with IHoP-siRNA (50 μg per each animal). The final group was injected with IHoP-siRNA after the onset of T1 D (blood glucose levels shown more than 300 mg/dL). All injections were performed via tail vein. Blood glucose levels were determined using a standard blood glucose meter (One touch profile, Johnson and Johnson Com., Milpitas, Calif.). Blood glucose levels were monitored every 2 days after injection until end of the experiment.

26. R. Alejandro, et al., *Diabetes* 31, 17 (1982).
27. Y. Kajimoto, et al., *Diabetologia* 42, 1417 (1999).
28. P. Maechler, et al., *J. Biol. Chem.* 274, 27905 (1999).
29. A. E. Butler, et al., *Diabetes.* 52, 102 (2003).
30. A. A. Elayat, et al., *J. Anat.* 186, 629 (1995).
31. N. Somoza, et al., *J. Immunol.* 153, 1360 (1994).
32. G. F. Bottazzo, et al., *N. Engl. J. Med.* 313, 353 (1993).
33. N. Itoh, et al., *J. Clin. Invest.* 92, 2313 (1993).
34. A. K. Foulis, et al., *Diabetologia* 30, 333 (1987).
35. A. K. Foulis and M. A. Farquharson, *Diabetes* 35, 1215 (1986).
36. A. Imagawa, et al., *J. autoimmune* 9, 391 (1996).
37. The authors thank Sun-Jeong Choi for her assistance with immunohistochemistry. This work was supported by National Institute of Health grants DK60015 and DK58614 awarded to BEP.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A method of ameliorating or delaying the onset of diabetes in a subject in need thereof, the method comprising administering a therapeutically effective amount of islet homeostasis protein (iHoP) modulating agent to said subject, wherein said iHoP modulating agent is a nucleic acid based inhibitor that targets an iHoP nucleic acid sequence.

2. The method of claim 1, wherein said iHoP modulating agent is administered via parenteral, ocular, oral, rectal, lingual, transdermal or intravaginal administration.

3. The method of claim 1, wherein said iHoP modulating agent is administered according to a regiment comprising daily dosage for a period of at least 24 hours, 48 hours, 3 days, 1 week or two weeks.

4. The method of claim 1, wherein said iHoP modulating agent is administered in a composition that comprises a pharmaceutically acceptable carrier.

5. The method of claim 1, wherein said patient in need exhibits at least one symptom comprising ketoacidosis, a state of metabolic dysregulation characterized by the smell of acetone; a rapid, deep breathing known as Kussmaul breathing; nausea; vomiting and abdominal pain; polyuria (frequent urination); polydipsia (increased thirst); polyphagia (increased hunger), increased or decreased insulin levels, or elevated serum glucose.

6. The method of claim 1, wherein said patient in need exhibits impaired glucose tolerance.

7. The method of claim 6, wherein said patient in need exhibits fasting glucose levels of 100 mg/dL to 125 mg/dL, or optionally fasting glucose levels above 125 mg/dL.

8. The method of claim 6, wherein said patient in need exhibits plasma glucose at or above 140 mg/dL (7.8 mmol/L), but not over 200 mg/dL (11.1 mmol/L), two hours after a 75 g oral glucose load.

9. A method of treating diabetes in a patient in need, said method comprising administering a therapeutically effective amount of a composition comprising an islet homeostasis protein (iHoP) modulating agent, wherein said iHoP modulating agent is a nucleic acid based inhibitor that targets an iHoP nucleic acid sequence.

10. The method of claim 9, wherein said iHoP modulating agent is administered via parenteral, ocular, oral, rectal, lingual, transdermal or intravaginal administration.

11. The method of claim 9, wherein said iHoP modulating agent is administered according to a regiment comprising daily dosage for a period of at least two weeks.

12. The method of claim 9, wherein said composition further comprises a pharmaceutically acceptable carrier.

13. The method of claim 9, wherein said patient in need exhibits one or more of the following symptoms:

Fasting plasma glucose level ≥7.0 mmol/L (126 mg/dL);

Plasma glucose ≥11.1 mmol/L (200 mg/dL) two hours after a 75 g oral glucose load as in a glucose tolerance test;

Symptoms of hyperglycemia and casual plasma glucose ≥11.1 mmol/L (200 mg/dL); or Glycated hemoglobin (Hb A1C) ≥6.5%.

14. The method of claim 13, wherein said patient in need exhibits two or more of the stated symptoms.

15. The method of claim 1, wherein the modulating agent is administered via introduction of a delivery vector to the patient.

16. The method of claim 1, wherein the modulating agent is an RNA interfering molecule targeting iHoP.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagttgaacc tggcctccat t                                              21
```

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttcaaggtc gtattcaccc a                                              21

<210> SEQ ID NO 3
<211> LENGTH: 627
<212> TYPE: PRT
<213> ORGANISM: Mus musculus

<400> SEQUENCE: 3
```

Met Ala Arg Gly Ser Val Ser Asp Glu Glu Met Met Glu Leu Arg Glu
1               5                   10                  15

Ala Phe Ala Lys Val Asp Thr Asp Gly Lys Gly Tyr Ile Ser Cys Asn
            20                  25                  30

Glu Leu Asn Asp Leu Phe Lys Ala Ala Cys Leu Pro Leu Pro Gly Tyr
        35                  40                  45

Arg Val Arg Glu Ile Thr Glu Asn Leu Met Ala Thr Gly Asp Leu Asp
    50                  55                  60

Gln Asp Gly Lys Ile Ser Phe Asp Glu Phe Ile Lys Val Phe His Gly
65                  70                  75                  80

Leu Lys Ser Thr Glu Val Ala Lys Thr Phe Arg Lys Ala Ile Asn Lys
                85                  90                  95

Lys Glu Gly Ile Cys Ala Ile Gly Gly Thr Ser Glu Gln Ser Ser Val
            100                 105                 110

Gly Thr Gln His Ser Tyr Ser Glu Glu Lys Tyr Ala Phe Val Asn
        115                 120                 125

Trp Ile Asn Lys Ala Leu Glu Asn Asp Pro Asp Cys Arg His Val Ile
    130                 135                 140

Pro Met Asn Pro Asn Thr Asp Asp Leu Phe Asn Ala Val Gly Asp Gly
145                 150                 155                 160

Ile Val Leu Cys Lys Met Ile Asn Leu Ser Val Pro Asp Thr Ile Asp
                165                 170                 175

Glu Arg Thr Ile Asn Lys Lys Lys Leu Thr Pro Phe Thr Ile Gln Glu
            180                 185                 190

Asn Leu Asn Leu Ala Leu Asn Ser Ala Ser Ala Ile Gly Cys His Val
        195                 200                 205

Val Asn Ile Gly Ala Glu Asp Leu Lys Glu Gly Lys Pro Tyr Leu Val
    210                 215                 220

Leu Gly Leu Leu Trp Gln Val Ile Lys Ile Gly Leu Phe Ala Asp Ile
225                 230                 235                 240

Glu Leu Ser Arg Asn Glu Ala Leu Ile Ala Leu Leu Arg Glu Gly Glu
                245                 250                 255

Ser Leu Glu Asp Leu Met Lys Leu Ser Pro Glu Glu Leu Leu Leu Arg
            260                 265                 270

Trp Ala Asn Tyr His Leu Glu Asn Ala Gly Cys Thr Lys Ile Thr Asn
        275                 280                 285

Phe Ser Thr Asp Ile Lys Asp Ser Lys Ala Tyr Tyr His Leu Leu Glu
    290                 295                 300

Gln Val Ala Pro Lys Gly Asp Glu Glu Gly Ile Pro Ala Val Val Ile
305                 310                 315                 320

```
Asp Met Ser Gly Leu Arg Glu Lys Asp Asp Ile Gln Arg Ala Glu Cys
            325                 330                 335

Met Leu Gln Gln Ala Glu Arg Leu Gly Cys Arg Gln Phe Val Thr Ala
            340                 345                 350

Thr Asp Val Val Arg Gly Asn Pro Lys Leu Asn Leu Ala Phe Ile Ala
            355                 360                 365

Asn Leu Phe Asn Lys Tyr Pro Ala Leu His Lys Pro Glu Asn Gln Asp
        370                 375                 380

Ile Asp Trp Gly Ala Leu Glu Gly Glu Thr Arg Glu Arg Thr Phe
385                 390                 395                 400

Arg Asn Trp Met Asn Ser Leu Gly Val Asn Pro Arg Val Asn His Leu
                405                 410                 415

Tyr Ser Asp Leu Ser Asp Ala Leu Val Ile Phe Gln Leu Tyr Glu Lys
                420                 425                 430

Ile Lys Val Pro Val Asp Trp Asn Arg Val Asn Lys Pro Pro Tyr Pro
                435                 440                 445

Lys Leu Gly Gly Asn Met Lys Lys Leu Glu Asn Cys Asn Tyr Ala Val
        450                 455                 460

Asp Leu Gly Lys Asn Gln Ala Lys Phe Ser Leu Val Gly Ile Ala Gly
465                 470                 475                 480

Gln Asp Leu Asn Glu Gly Asn Arg Thr Leu Thr Leu Ala Leu Val Trp
                485                 490                 495

Gln Leu Met Arg Arg Tyr Thr Leu Asn Ile Leu Glu Asp Ile Gly Gly
                500                 505                 510

Gly Gln Lys Val Asn Asp Asp Ile Ile Val Asn Trp Val Asn Thr Thr
        515                 520                 525

Leu Lys Glu Ala Gln Lys Ser Ser Ser Ile Ala Ser Phe Lys Asp Pro
530                 535                 540

Lys Ile Ser Thr Ser Leu Pro Val Leu Asp Leu Ile Asp Ala Ile Gln
545                 550                 555                 560

Pro Gly Ser Ile Asn Tyr Asp Leu Leu Lys Thr Glu Asn Leu Asp Asp
                565                 570                 575

Glu Glu Lys Leu Asn Asn Ala Lys Tyr Ala Ile Ser Met Ala Arg Lys
                580                 585                 590

Ile Gly Ala Arg Val Tyr Ala Leu Pro Glu Asp Leu Val Glu Val Asn
                595                 600                 605

Pro Lys Met Val Met Thr Val Phe Ala Cys Leu Met Gly Lys Gly Met
        610                 615                 620

Lys Arg Val
625

<210> SEQ ID NO 4
<211> LENGTH: 2228
<212> TYPE: DNA
<213> ORGANISM: Mus musculus

<400> SEQUENCE: 4
gtagatctga aggactgggg tttctgacca cacagcagtg ctgctgacac agaggacagt    60
ttctctacca ggtctgtcac ctaaagcagt gaaaatggcc agaggatccg tgtctgacga   120
agaaatgatg gagctcagag aggcttttgc caaagttgat accgatggca aggatacat    180 cagctgcaat gagctaaatg acttgttcaa ggccgcctgc ctgcctctgc ctgggtaccg   240
agtgagagaa atcacagaaa acctgatggc cacaggtgat ctggaccaag atggaaagat   300
```

```
cagctttgat gagtttatca aggtcttcca tggcttaaaa agcaccgagg ttgccaaaac    360
cttccgaaaa gctatcaaca agaaggaagg gatctgtgcg attggcggca cctctgagca    420
gtccagcgtt ggtacccagc actcttactc agaggaagaa aagtatgcct ttgtcaactg    480
gataaacaaa gccctggaga atgacccccga ctgccggcat gtcatcccca tgaaccccaa    540
caccgacgat ctcttcaatg ctgtaggcga tggcatagtt ctttgtaaaa tgatcaacct    600
gtctgtgcca gacacgattg acgagagaac gatcaacaag aaaaagctca caccattcac    660
cattcaggaa aacttgaact tggctctgaa ctctgcctct gccattgggt gccacgtggt    720
taatataggg gccgaggacc tgaaggaggg caagccttac ctggtcctgg gacttttgtg    780
gcaagtcatc aagattgggt tgtttgctga cattgaactc agcagaaatg aagctctgat    840 tgctctttg agagaaggag agagcctaga ggatttgatg aagttgtctc ctgaagaact    900
cctgctgcgg tgggctaact accacctaga aaacgcaggc tgcaccaaaa tcaccaactt    960
cagcaccgac atcaaggact ccaaagctta ttaccacctg ctcgagcaag tggctccaaa   1020
aggagatgaa gaagggatcc cggcggttgt gattgacatg tcaggactga gggagaagga   1080
tgacatccag agggcagagt gcatgctgca acaggcggag aggctgggct gccggcagtt   1140
tgtcacagct actgatgttg tccgagggaa ccccaagttg aacctggcct tcattgccaa   1200
cctcttcaac aaatacccctg ccttacacaa accagagaac caggacattg actgggggggc   1260 tctcgaaggt gagacgaggg aagagcggac cttcaggaat tggatgaact ccctgggcgt   1320
taacccgcgc gtcaatcact tgtacagcga cttatcggat gccttagtca tcttccagct   1380
ctatgagaag atcaaagtcc ctgttgattg aacagagta aacaagcctc cataccccaa   1440
gctggggggc aatatgaaaa agctggagaa ctgtaattat gcagtggacc tggggaagaa   1500
tcaagctaaa ttctccctgg ttggcatcgc aggacaagac ctcaatgaag gaaaccgaac   1560
tctcacgctg gcattggttt ggcagctcat gagaaggtac acactgaata tcctggaaga   1620
tatcggaggt ggacagaagg tcaatgatga cattattgtc aactgggtga atacgacctt   1680
gaaggaggca cagaaaagct catccattgc tagcttcaag gacccaaaga tcagtaccag   1740
cctcccggtt ctggatctca ttgacgccat tcagccaggt tccataaact atgaccttct   1800
aaagacagaa aacctggatg atgaagagaa actcaacaat gcaaagtatg ccatctctat   1860
ggccagaaaa atcggagcaa gggtgtacgc cctcccagaa gacctggttg aagtgaaccc   1920
caaaatggtc atgacagtgt ttgcctgcct catggggaaa gggatgaaga gggtgtaagt   1980
cccagaggag taagccagaa atcgacacag acaagcctga gggggtcagc acatggtgct   2040
cccaggatgc agaggaccat tcaagccatt gcaaagtcct gaaccttgga gacattattt   2100
gaaattcaca catttcttca gccaagtagc ttctgctata attagcaata cgtgcttctc   2160
ttttgttgtt gtttttttcag aagatgtact cgcctacaaa ttttttttttt attctttgaa   2220 agtctacc                                                            2228
```